(12) United States Patent
Kronholm et al.

(10) Patent No.: US 10,239,839 B2
(45) Date of Patent: *Mar. 26, 2019

(54) COMPOUNDS AND FORMULATIONS SUITABLE FOR RADICAL SCAVENGING

(71) Applicant: Solenne BV, Groningen (NL)

(72) Inventors: David F. Kronholm, Loudon, TN (US); Alexander B. Sieval, Groningen (NL); Jan C. Hummelen, Groningen (NL)

(73) Assignee: Solenne BV (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/333,766

(22) Filed: Oct. 25, 2016

(65) Prior Publication Data

US 2017/0037012 A1 Feb. 9, 2017

Related U.S. Application Data

(60) Division of application No. 14/076,612, filed on Nov. 11, 2013, now Pat. No. 9,475,810, which is a continuation of application No. 12/516,992, filed as application No. PCT/US2007/085879 on Nov. 29, 2007, now Pat. No. 8,580,810.

(60) Provisional application No. 60/861,697, filed on Nov. 29, 2006.

(51) Int. Cl.
| | | |
|---|---|---|
| C07D 221/02 | (2006.01) | |
| C07D 221/18 | (2006.01) | |
| C07D 471/06 | (2006.01) | |
| A61K 8/49 | (2006.01) | |
| A61Q 19/00 | (2006.01) | |

(52) U.S. Cl.
CPC .......... *C07D 221/18* (2013.01); *A61K 8/4926* (2013.01); *A61Q 19/00* (2013.01); *A61Q 19/004* (2013.01); *C07D 471/06* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 5,380,703 A | 1/1995 | Kao et al. | |
| 5,648,523 A | 7/1997 | Chiang | |
| 7,189,681 B2 | 3/2007 | Miyamoto | |
| 7,547,926 B2 | 6/2009 | Setayesh et al. | |
| 2005/0058675 A1 | 3/2005 | Wilson et al. | |
| 2005/0136079 A1 | 6/2005 | Burangulov et al. | |
| 2005/0239717 A1 | 10/2005 | Kronholm et al. | |
| 2005/0245606 A1 | 11/2005 | Kronholm et al. | |

FOREIGN PATENT DOCUMENTS

JP 2002255966 A 9/2002

OTHER PUBLICATIONS

Benedetto, A.F. et al., "Unusual Triplet State Relation in $C_{60}$ Oxide," Chemical Physics Letters, 310:25-30 (1999).
Brabec et al., "Origin of the Open Circuit Voltage of Plastic Solar Cells," Advanced Functional Materials, 11(5):374-380 (2001).
Hamano, T. et al., "Singlet Oxygen Production from Fullerene Derivatives: Effect of Sequential Functionalization of the Fullerene Core," Chemistry Commun., 21-22 (1997).
Hummelen et al., "Isolation of the Heterofullerene $C_{59}N$ as Its Dimer $(C_{59}N)_2$," Science, 269:1554-1556 (1995).
Hummelen, J.C. et al., "Resolution and Circular Dichroism of an Asymmetrically Cage-Opened [60] Fullerene Derivative," Chem. Commun., 3:281-282 (1998).
Hummelen, J.C. et al., "There is a Hole in my Bucky," *Journal of the American Chemical Society* 117: 7003-7004 (1995).
International Search Report for PCT/US07/085879 dated May 8, 2008.
Iwamatsu, S. et al., "$H_2O$©open-cage Fullerene $C_{60}$: Control of the Encapsulation Property and the First Mass Spectroscopic Identification," Tetrahedron Letters, 45:6391-6394 (2004).
Le Strat et al., "The Solubility of Some Azafullerene Derivatives," Fullernene Science and Technology, 7(5):757-768 (1999).
Supplementary European Search Report for EP 07 86 4876 completed on Apr. 8, 2011.
Tagmatarchis, K.O. et al., "Synthesis and Spectroscopic Characterization of the Second Isomer $(C_{69}N)_2$ (II) Heterofullerene," Synlett, 12:1761-1764 (2000).
Vougioukalakis, G.C. et al., "Novel Open-Cage Fullerenes Having a 12-Membered-Ring Orifice: Removal of the Organic Addends from the Rim of the Orifice," Organic Letters, 6(8):1245-1247 (2004).
Vougloukalakis, G.C. et al., Open-Cage Fullerene Derivatives with 15-Membered-Ring Orifices, J. Org. Chem., 69:4524-4526 (2004).

*Primary Examiner* — Noble E Jarrell
(74) *Attorney, Agent, or Firm* — Foley Hoag LLP

(57) ABSTRACT

The present invention relates to compositions and methods of using free radical scavengers with reduced $^1O_2$ generation. In certain embodiments, these compositions and methods of use relate to fullerene-derived ketolactams and fullerene-derived ketolactam derivatives, fullerene derivatives, and/or fullerenes. In yet other embodiments, the invention relates to cosmetic or dermatological compositions comprising said free radical scavengers with reduced $^1O_2$ generation.

17 Claims, 15 Drawing Sheets

Molecule 1

Molecule 3                    Molecule 2

[a]

[b]

[B]

KetoEster1

COMPOUNDS AND FORMULATIONS SUITABLE FOR RADICAL SCAVENGING

RELATED APPLICATIONS

This application is a divisional of U.S. patent application Ser. No. 14/076,612, filed Nov. 11, 2013, now U.S. Pat. No. 9,475,810, which is a continuation of U.S. patent application Ser. No. 12/516,992, filed Jun. 17, 2010, now U.S. Pat. No. 8,580,810, which is a § 371 national stage application based on Patent Cooperation Treaty Application serial number PCT/US2007/085879, filed Nov. 29, 2007, which claims the benefit of priority to U.S. Provisional Patent Application Ser. No. 60/861,697, filed Nov. 29, 2006.

BACKGROUND OF THE INVENTION

It is well known in the art that fullerenes (such as, for example, $C_{60}$, $C_{70}$, $C_{76}$, $C_{78}$, and $C_{84}$), which are closed-cage all-carbon molecules, and chemical derivatives of fullerenes react with a wide variety of free radical species (OH., NO., ROO., .aryl, .alkyl, etc.) and thus have potential in various applications, including biological applications, where the reduction of free radical species, such as reactive oxygen species (ROS), is desired (Krusic, P. J. et al., Science, 254, 1183-1185, 1991; Dugan, L. et al., Proc. Natl. Acad. Sci., 94, 9434-9439, 1997; Lee, Y. T. et al., Proc. Soc. Exp. Bio. And Med., 224, 69-75, 2000). ROS are known to contribute to cell damage and/or cell death, as well as having a role in various metabolic and immune system processes. Reduction in the concentration of one or more radical species in a biological environment thus has benefits in various biological environments for amelioration of a host of conditions. One example is the reduction of OH., ROO. (peroxyl) and other radical species concentrations around and in cell membranes so as to protect the cell membrane and its components from oxidative damage, such as DNA cleavage and/or mutation, loss of cell wall integrity which can lead to death of the cell, or other undesired consequences of elevated concentrations of ROS. Another example is that supplementation with antioxidants may allow conservation of biological antioxidant compounds that occur naturally in humans and animals, such as Vitamin E, Vitamin C, or others, which are consumed by ROS. Such free radical scavengers or in the case where the free radical species are oxidizing species, antioxidants (free radical scavenger and antioxidant will be used interchangeably in the present document), protection mechanisms occur naturally in biological environments through the activity of Vitamin E, Vitamin C, Coenzyme Q10, and other compounds, which react with free radical species, and go through various regeneration processes, reducing concentrations of free radical species. In many cases it is desirable to augment these naturally occurring protection mechanisms through supplementation with a free radical scavenger.

Antioxidants have been shown to have efficacy in particular as protectants and/or remediative agents in dermatological and cosmetics applications. Vitamin E, Vitamin C, Coenzyme Q10, naturally occurring antioxidants, such as polyphenolics derived from fruit seeds and skin (grape, cranberry, tomato, etc.), and synthetic compounds are used extensively for the purpose of protection of the skin (human and animal) from oxidative stress caused by exposure to light, pollution, cigarette smoke and other sources of free radicals, as well as endogenous sources, such as normal metabolic processes and immune system responses that generate free radicals. Antioxidants are known as well as to promote the general healthy appearance of the skin. Antioxidants also can play a role in the remediation of the appearance of inflammatory conditions of the skin, reduction in damage incurred to the skin by inflammation, and promote the healing of inflammatory conditions of the skin, through the reduction of concentration of free radicals produced by the immune system, such as superoxide, nitric oxide, and hydrogen peroxide, for example, caused by the respiratory burst of neutrophils in response to bacteria or other stimuli to the immune system.

The rate of formation of new extracellular matrix, such as collagen, in the skin is also thought to be increased (or the process of extracellular matrix breakdown is decreased) through the use of for example Vitamin C and retinoid antioxidants, and the process of new extracellular matrix formation or conservation of extracellular matrix in the skin is enhanced through the use of antioxidants.

In addition antioxidants are taken as oral supplements to protect against oxidative damage or other consequences of ROS or other free radicals to the skin and other biological substrates, such as neuronal cells, build-up of arterial plaque, prevention of cell apoptosis, inflammatory conditions, such as sepsis, and extension of life-span, among other uses. Conditions thought to be caused or exacerbated by excess ROS and resulting oxidative damage include, but are not limited to atherosclerosis, cancer, and neurological disorders, such as Alzheimer's disease and Parkinson's disease.

Commonly used antioxidant compounds as listed above, such as Vitamin E, Vitamin C, Coenzyme Q10, carotenoids, and plant derived polyphenols have various drawbacks, such as in some cases limited transport to and through biological environments, instability when exposed to light and air, and less than desired efficacy when applied as supplements. One drawback of many commonly used natural and synthetic antioxidants is that they can in some cases have minimal efficacy or even have pro-oxidant activity due to the fact that they themselves become free radicals after reacting with a free radical. This can lead to undesired effects, such as localized accumulation of the oxidized free radical analogues of the antioxidant and reaction with biological media, such as cells, if, for example, these antioxidants are not regenerated with complementary species (e.g., Vitamin E regenerated by Vitamin C). Vitamin E and other natural antioxidants must be regenerated via reaction with other antioxidants. Thus, supplementation with only one or several naturally occurring antioxidants may have reduced or little efficacy, or even pro-oxidant activity in some cases since the entire reaction network necessary for recycling of the individual antioxidants may not be sufficient to regenerate the supplemented antioxidants. It would thus be desirable to provide an antioxidant supplement which did not become a potentially reactive free radical species upon reaction with free radicals.

Fullerenes are known to generate addition products with radicals that are relatively stable and unreactive. The chemical reactivity of fullerenes with free radicals is via addition reactions of the free radicals with the C=C double bonds of the fullerene cage. Since multiple radicals can react with a single fullerene molecule (3, 6, 12, 16, or more free radicals per fullerene molecule), it is possible that the radical electrons can pair and thus be neutralized. Fullerenes thus have very desirable properties as free radical scavenging and antioxidant supplements to biological systems.

A drawback however to the use of fullerenes as free radical scavengers, especially in protection of biological environments against ROS, is the well-known property of fullerenes, especially $C_{60}$ and $C_{70}$, to produce singlet-oxygen, $^1O_2$. Arbogast, J. W. et al., J. Phys. Chem., 95, 11, 1991. This occurs via photoexcitation of the fullerene or fullerene derivative and generation of the excited triplet state which then transfers energy to diatomic oxygen molecules to form $^1O_2$ through the so-called Type 1 mechanism. It is also believed that the Type 2 mechanism may occur for some fullerene compounds whereby electrons are transferred to fullerenes and then to dissolved $O_2$, leading to superoxide anion ($O_2^-$.). Yamakoshi, Y. et al., J. A. Chem. Soc., 125, 42, 2003. In both cases the triplet excited state of the fullerene, which is in most cases relatively long-lived, is generated and leads to the formation of either $^1O_2$, $O_2^-$., or other products. $^1O_2$ and $O_2^-$. are themselves ROS that can lead to damage to biological substrates and are thus undesirable in the case where it is desired to reduce or minimize concentrations of ROS.

Triplet state and $^1O_2$ quantum yields have been measured for native (underivatized) fullerenes and have been shown to be approximately 1.0 for $C_{60}$, $C_{70}$, and $C_{78}$, and lower for $C_{76}$ and $C_{84}$ (between about 0.2 and 0.3). Juha, L. et al., Chem. Phys. Lett., 335, 5, 539-544, 2001. Fullerene derivatives preserve this property to varying degrees, with multi-substituted fullerene derivatives showing in some cases reduced $^1O_2$ generation capacity, though still significant. Hamano, T. et al., Chem Commun. 21-22, 1997.

Ideally, a photosensitizer has good absorption in the visible wavelengths combined with a high $^1O_2$ quantum yield, among other characteristics. $C_{60}$ is not a very good absorber relative to commonly used photosensitizers, such as methylene blue in the visible wavelengths, but $C_{70}$, $C_{76}$, $C_{78}$, and $C_{84}$ are significantly better absorbers in the visible wavelengths, and this augments the overall photosensitizing capacity. In the case of $C_{76}$ and $C_{84}$, this higher light absorption offsets the lower triplet state and $^1O_2$ quantum yield in terms of photosensitizing capacity. Therefore, even for the fullerenes $C_{76}$ and $C_{84}$, which have a lower singlet oxygen quantum yield compared to $C_{60}$ and $C_{70}$, it would be desirable to reduce the singlet oxygen quantum yield.

In many applications, especially biological applications, it would be desirable to minimize the generation of $^1O_2$ but preserve the inherent capacity of the fullerene cage to react with free radicals, while maintaining a relatively low intrinsic optical absorption (i.e., molar extinction coefficient).

Fullerene-derived ketolactam derivatives of fullerenes (FIG. 1, Molecule 1) were first reported in 1995 by Hummelen et al. Hummelen, J. C. et al., J. Am. Chem. Soc., 117, 26, 1995.

Later it was shown that these fullerene-derived ketolactam compounds could be used as intermediates to prepare $(C_{59}N)_2$ which in turn could be used as a precursor to prepare $C_{59}NH$ and $RC_{59}N$ azaheterofullerene derivatives. Hummelen, J. C. et al., Science, 269, 1554, 1995. The impetus for the preparation of these compounds was for application as superconductors, organic ferromagnetism, and photoelectric components (n-type semiconductors in photodiodes). Ketolactams were also derived from $C_{70}$, and in an analogous fashion, ketolactam derivatives of fullerenes $C_{76}$, $C_{78}$, $C_{84}$ and other higher fullerenes can also be prepared. Hummelen, et al., Topics in Current Chemistry, Springer Verlag, Vol. 199, 1999.

Tagmatarchis reported that $(C_{59}N)_2$ and $C_{59}NH$ showed reduced $^1O_2$ quantum yields and hypothesized that this was due to alteration of the electronic structure of the fullerene cage by inclusion of the N heteroatom in the fullerene cage. Tagmatarchis, N. et al., J. Org. Chem., 66, 8026-8029, 2001.

Hauke et al., further confirmed that a series of $RC_{59}N$ compounds showed reduced $^1O_2$ quantum yields. Hauke, F. et al., Chemistry, 12, 18, 4813-4820, 2006. These compounds were prepared beginning with the $(C_{59}N)_2$ dimer synthesized with the keto-lactam intermediate. Hauke et al. showed through experimental measurements that the nature of the R group significantly affected the $^1O_2$ quantum yield, which for the compounds with the lowest $^1O_2$ quantum yield was about half the $^1O_2$ quantum yield of $C_{59}NH$, which is a significant change. No explanation is given for why the R group affects the triplet state and $^1O_2$ quantum yields. Further, no consideration or conjecture on the triplet state and $^1O_2$ quantum yield properties of fullerene-derived ketolactams was given.

Other fullerene-derived ketolactam derivatives were later prepared for use as n-type semiconductors in organic photovoltaics. Brabec, C. et al., Adv. Funct. Mater., 11, 5, 2001. None of the work with fullerene-derived ketolactams to date in the art has considered the triplet state or $^1O_2$ quantum yields of fullerene-derived ketolactams, nor envisioned the use of these compounds as free radical scavengers or as potentially generating less $^1O_2$ than fullerenes and/or fullerene derivatives.

SUMMARY OF THE INVENTION

It is one object of the present invention to provide for a fullerene-derived radical scavenger with reduced production of $^1O_2$ and/or other products resulting from the photogenerated triplet state of fullerenes, while maintaining to a desirable degree the relatively low optical absorption properties and the ability for the fullerene-derived moiety to react with free radicals.

In some embodiments, these fullerene-derived radical scavengers are fullerene-derived ketolactams and fullerene-derived ketolactam derivatives. In certain embodiments, the fullerene-derived radical scavengers may comprise one or more ketolactam modifications of the fullerene cage. Other embodiments may include the chemical bonding of one or more addends to the fullerene cage, forming fullerene-derived ketolactam methano derivatives, fullerene-derived ketolactam pyrrolidine derivatives, fullerene-derived ketolactam epoxide derivatives, methanofullerene derivatives, pyrrolidine fullerene derivatives, or epoxide fullerene derivatives, or other fullerene-derived ketolactam derivatives or fullerene derivatives.

It is another object of the present invention to provide for formulations comprising antioxidants. In some embodiments, these formulations may be used on the skin of an animal or human. In certain embodiments, these formulations may be used to reduce the concentration of free radicals in the skin of an animal or human and/or to reduce the generation and/or concentration of singlet oxygen or superoxide in the skin of an animal or human. In certain embodiments, these formulations may be used to reduce the concentration of photoexcited triplet states of fullerenes, fullerene derivatives, or fullerene-derived ketolactams in the skin of an animal or human and/or to reduce the generation and/or concentration of singlet oxygen or superoxide in the skin of an animal or human. In certain embodiments, the formulations may be used for the treatment of inflammatory conditions, including acne, psoriasis, eczema, rosacea, sunburn, allergic response, sepsis, dermatomyositis, radiation induced erythema, chemically induced erythema, thermal burn, or laser induced erythema. One of skill in the art would readily recognize that other inflammatory conditions may be treated using the compounds and methods of the present invention.

It is yet another object of the present invention to provide compounds for improving the stability of a formulation by reducing the concentration of photoexcited triplet states of fullerenes, fullerene derivatives, or fullerene-derived ketolactams and/or reducing the generation and/or concentration of singlet oxygen or superoxide in a formulation containing a fullerene, fullerene derivative, or fullerene-derived ketolactam.

It is another object of the present invention to provide for formulations comprising fullerenes, fullerene derivatives, or fullerene-derived ketolactams which have a reduced propensity for photooxidation by reduction in the optical transmittance of the formulation.

It is still another object of the present invention to provide compounds for use as semiconductors.

DETAILED DESCRIPTION OF THE INVENTION

Figure 2:
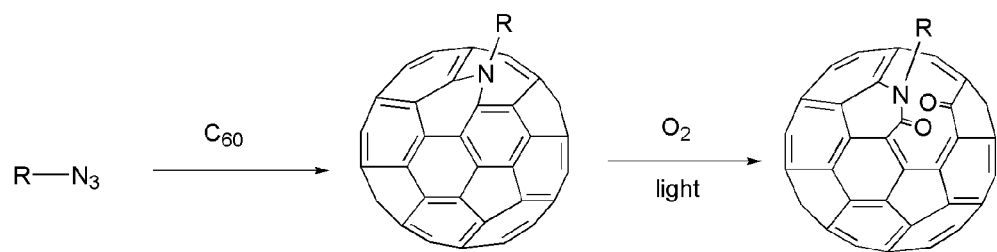
FIG. 2 depicts a general reaction scheme for the preparation of fullerene-ketolactam compounds.

One object of the present invention is to provide for a fullerene-derived radical scavenger with reduced $^1O_2$ and/or other products resulting from the photogenerated triplet state of fullerenes, while maintaining to a desirable degree the relatively low optical absorption properties and the ability for the fullerene-derived moiety to react with free radicals. "Fullerene-derived ketolactam" refers to a ketolactam molecule formed by cage-opening of a fullerene, as shown in FIG. 2. Fullerene-derived ketolactam molecules, as described herein, are not termed fullerenes or fullerene derivatives, since the term "fullerene" refers to a close-caged, all carbon molecule, and the carbon cage has been opened in the case of fullerene-derived ketolactams.

It has been found in the present work that $C_{60}$ fullerene-derived ketolactam derivatives have a capacity for generation of $^1O_2$ which is significantly less than $C_{60}$ and common $C_{60}$ derivatives, while maintaining a similar, low optical absorption profile, and thus fullerene-derived ketolactams are suitable for use in applications where less generation of $^1O_2$ is desirable than is possible with fullerenes or other fullerene derivatives. Since the majority of the fullerene cage is unmodified, the molecules of the present invention react with free radicals with a desirable efficacy.

Certain compounds of the present invention are based on modification of the fullerene cage to give open-cage ketolactams, with various functional moieties to provide alterations in physical and chemical properties.

One general method for the preparation of fullerene-derived ketolactams is by oxidation of [5,6]-azafulleroid derivatives (J. C. Hummelen et al., J. Am. Chem. Soc. 1995, 117, 7003). These latter compounds are obtained by addition of an azide derivative to a fullerene. This reaction is well known and a large variety of azafulleroids has been prepared (A. Hirsch and M. Brettreich, Fullerenes: Chemistry and Reactions. Wiley-VCH, 2005, Weinheim, Germany). The general reaction scheme is depicted in FIG. 2.

Figure 3:
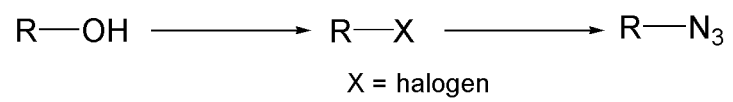
FIG. 3 depicts a common synthetic route for the preparation of azides.

It has been demonstrated that functional groups, such as ether groups and ester groups, can be present in the azide derivative used in the addition reaction. The preparation of azide derivatives is well known in the art, as is their reactivity. (See, for example: a) The chemistry of the azide group, S. Patai (Ed.), Wiley, New York, 1971; and b) The chemistry of functional groups, Supplement D: the chemistry of halides, pseudo-halides and azides, S. Patai and R. Rappoport (eds.), J. Wiley and Sons, New York 1983.) A general scheme which can be used as a guideline for the preparation of the azide derivatives is depicted in FIG. 3. Protection of certain functional groups may be required in some cases A common route for the synthesis of azides is by (nucleophilic) substitution of halogen atoms using sodium azide, as is demonstrated in the synthesis of HG2-V1. A large variety of functional groups can be present in this substitution reaction without causing problems. However, other methods for the preparation of azides exist, the use of which can be required if the substitution reaction leads to undesired side reactions.

A large number of halogen-containing organic compounds are commercially available or can be easily prepared. The commercial compounds include derivatives, such as halogen-containing carboxylic acids, halogen-containing carboxylic esters, and halogen-containing alkyl-aryl compounds, all of which are suitable starting materials for the preparation of the fullerene-ketolactams as described in the present invention. In addition, a large variety of alcohols are known in literature or commercially available, which can be converted into the desired halogen derivatives by various methods, such as by the reaction with thionyl chloride, as is described in Example 1.

Figure 4:
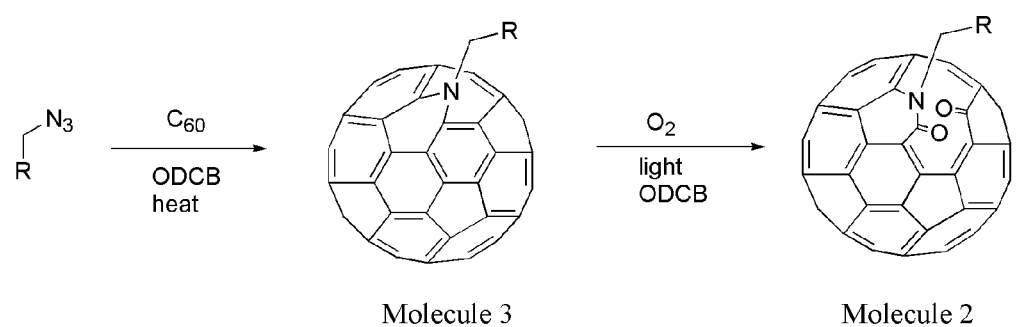
FIG. 4 depicts one possible synthetic scheme for the compounds of the present invention.

An example synthetic scheme for the compounds of the present invention is outlined in FIG. 4. Azide compounds are reacted with $C_{60}$, and the resulting intermediate is then activated with light in the presence of oxygen to convert the intermediate compound to the final open-cage fullerene-derived ketolactam compound, analogous to previously published syntheses (C. J. Brabec et al., *Advanced Functional Materials* 2001, 11, 374).

The wide selection available for the R group allows for the present fullerene-derived ketolactam compounds to be chemically derivatized in a wide variety to provide variations in chemical and physical properties, such as but not limited to solubility, bio-transport, and/or chemical reactivity. The choice of different R addends may also provide alterations in the triplet and $^1O_2$ quantum yields, and may be chosen so as to optimize the triplet and $^1O_2$ quantum yields and/or light absorption properties to alter the overall photosensitizing properties.

R-addends may be chosen that give additional reactivity, such as radical scavenging ability, e.g., conjugated alkenes, such as carotenoids, or hydrogen-donating antioxidant moieties. Dyads may be created where the R-addend participates in electron transfer with the fullerenic moiety of the fullerene-derived ketolactam, e.g., porphyrin dyads may be prepared.

The fullerene-derived ketolactams of the present invention may also be prepared from $C_{70}$, $C_{76}$, $C_{78}$, $C_{84}$ or other fullerenes, by using the analogous reaction chemistry as described here for $C_{60}$. Mixtures comprising two or more of the following: $C_{60}$-fullerene-derived ketolactam, $C_{70}$-fullerene-derived ketolactam, $C_{76}$-fullerene-derived ketolactam, $C_{78}$-fullerene-derived ketolactam, $C_{84}$-fullerene-derived ketolactam, and $C_{90}$-fullerene-derived ketolactam, may be synthesized by using mixtures of the corresponding fullerenes in place of pure fullerenes, and the resulting mixtures of fullerene-derived ketolactams may subsequently be used in any of the radical scavenging applications, such as skin care formulations, or other applications described herein. The different fullerenes or fullerene derivatives may be in any proportion, but typically the composition (relative to fullerene-derived ketolactam content) would be 60%-90% of $C_{60}$-fullerene-derived ketolactam, 10%-40% $C_{70}$-fullerene-derived ketolactam, and 1%-20% fullerene-derived ketolactam based on fullerenes higher in molecular weight than $C_{60}$. See PCT/US07/72965 for descriptions of methods of synthesis of such mixtures.

In addition, mono-, bis-, or multi-adducts may be made which, in addition to the ketolactam moiety, may consist of one or more other addends bonded directly to the fullerenic carbons. For example, Molecule 2 (FIG. 4) may be used as a pre-cursor to the well-known diazoalkane addition chemistry (Hummelen, J. C. et al., J. Org. Chem., 60, 532-538, 1995) to form an adduct consisting of Molecule 2 with an additional phenyl-$C_n$-butyric-acid methyl-ester (PCBM) unit or other methanofullerene unit attached in one or more locations of the spherical fullerene moiety. In a similar fashion, so-called Prato adducts consisting of pyrrolidine addends (Maggini, M. et al., J. Am. Chem. Soc., 115(21), 9798-9799, 1993) may be added in addition to the ketolactam group. Further, epoxide adducts to the fullerene cage, formed by photochemical (Schuster, D. et al., Chem. Commun., 2493-2494, 1998) or other means, may be included in addition to the ketolactam group. Molecule 2 may be used as a precursor to synthesize the aforementioned mono-, bis-, or multi-adducts, or the methanofullerene, pyrrolidine or epoxide fullerene derivatives may be prepared and substituted for the $C_{60}$ reactant of FIG. 4. Further, the addition of one or more adducts to the fullerene-derived ketolactams of the present invention can lead to even further reduced capacity for generation of $^1O_2$, since it has been shown that with the increase of addends, such as epoxides to the fullerene core, the capacity for production of $^1O_2$ decreases (Hamano, T. et al., Chem Commun. 21-22, 1997).

In the case of fullerene epoxides, fullerene derivative epoxides, or fullerene-derived ketolactam epoxides (such as the mono-, bis-, or multi-adduct compounds described above), it is also known that the epoxides are efficient quenchers of the fullerene, fullerene derivative, or fullerene-derived ketolactam photoexcited triplet state (Benedetto, A. F., Chemical Physics Letters, 310, 1999, 25-30), and data presented herein shows that this leads to a net generation of singlet oxygen much reduced from the expected values based on the quantum yield of singlet oxygen generation for fullerenes and fullerene derivatives. Therefore, it is an object of the present invention to use epoxidized versions of a fullerene, fullerene derivative, or fullerene-derived ketolactam, which can be prepared for example by the exposure of said fullerene, fullerene derivative, or fullerene-derived ketolactam to light and air, and included in a sufficient concentration to a formulation intended for use in skin care to preserve the formulation from photooxidation, and/or to minimize the formation of singlet oxygen and/or superoxide on or in the skin. Such epoxides of fullerenes, fullerene derivatives or fullerene-derived ketolactams, which act to quench photoexcited states may also be used to reduce the concentration of superoxide or singlet oxygen directly via energy or electron transfer between the epoxide compound and singlet oxygen or superoxide.

It is also envisioned that the addition of the ketolactam moiety directly to the fullerene cage may give an advantage in the eventual breakdown of the fullerene cage in metabolic and/or environmental processes. Reaction with, for example, enzymes specific for keto- and lactam-groups may occur or other reactions with the additional keto- and lactam-oxygens, which may allow for easier degradation of the fullerene cage.

Addition of long-chain straight or branched alkane, conjugated alkene or alkene units, such as $R=C_{22}H_{45}$ or $C_{16}H_{33}$ (or alkoxy units, such as $R=OC_{22}H_{45}$ or $R=OC_{16}H_{33}$) are of interest for application in skincare since they confer lipophilicity, which is desirable from the standpoint of transport to and/or through the stratum corneum, and subsequent location in lipophilic regions of biological environments, such as cell walls. Lipophilicity also allows convenient formulation in lipophilic ingredients, such as oils, waxes, or wax-esters or other lipophilic compounds which are commonly used in the art to create formulations for application to the skin. In some applications, for example in use as an internal medication, more or less lipophilicity may be desired, or hydrophilicity may be desired. In the cases where hydrophilicity is desired, glycolic or other polar units may be used as addends.

The compounds of the present invention are envisioned for use as antioxidants (or radical scavengers) in a range of applications where antioxidants are commonly used, including but not limited to, skin care (cosmetic and dermatological), use as a pharmaceutical compound to ameliorate or prevent conditions associated with oxidative stress, such as but not limited to, neurological disorders, heart disease, disorders associated with inflammation, etc. The compound of the present invention may also be used as antioxidants in non-health related uses, such as polymer stabilizers, food preservatives, and the like.

The compound of the present invention are also envisioned for use to ameliorate conditions associated with inflammation, such as caused by the production of reactive oxygen species or other radical species by such immune system components as neutrophils. The compounds of the present invention, by scavenging such radical species produced by the immune system, may thus mediate, prevent, or ameliorate immune system responses.

The compounds of the present invention may be used in topical compositions which also comprise a cosmetically and/or dermatologically acceptable carrier. The phrase "cosmetically and/or dermatologically acceptable carrier," as used herein, means that the carrier is suitable for topical application to the keratinous tissue, which includes safety for use in topical application and compatibility with the actives (fullerene-derived ketolactams) of the present invention.

A safe and effective amount of carrier is from about 50% to about 99.999%, from about 60% to about 99.99%, from about 70% to about 99.9%, or from about 80% to about 99% of the composition, all said percentages referring to weight percent.

The active of the present invention may be either dissolved or suspended as a solid particulate in the carrier. The active may be dissolved in one or more phases of the carrier, with only a small amount of the active present as a suspended solid particulate. In certain embodiments, there is no measurable amount of active present as a suspended solid particulate.

The carrier used in the present invention can be any of a wide variety of forms, such as are commonly used in the art. Examples include but are not limited to simple solutions (water or oil based), emulsions (creams, lotions) and solid forms (gels, sticks). Emulsion carriers, such as commonly used in the art to make for example creams or lotions include, but are not limited to, oil-in-water, water-in-oil, water-in-oil-in-water, and oil-in-water-in-silicone emulsions.

In the case where the carrier is an emulsion and the active is dissolved in the carrier, it is well known in the art that the active will distribute in either the oil or water phase, depending on whether the active is oil soluble or water soluble, or in the case where the active is soluble in both oil and water (amphiphilic), or the active is present as a suspended solid, the active may distribute in both the oil and water phases, in a proportion depending on the relative solubilities in each phase.

The actives as described herein may be used as a particulate component of formulations which do or do not contain a liquid phase, such as solid or liquid makeup formulations.

A "polar compound" as used herein refers to hydrophilic or amphiphilic compounds which dissolve in varying degrees in water. Polar compounds may be used to dissolve or solubilize an active of the instant invention, or otherwise provide a hydrophilic or amphiphilc component of the carrier for an active of the present invention, with or without an oily phase present in the formulation, to form single phase or multi-phase (emulsion) formulations, and with or without other ingredients in the formulation as described herein. Examples of such polar compounds are water, alcohols, mixtures of waters and alcohols, hydrogels consisting of water and alcohol components with a gelling agent, and other hydrophilic compounds as are typically used either alone or in combination with an oily phase to form single phase formulations or bi-phasic emulsions. Examples of such bi-phasic formulations are lotions and creams. Other examples of polar compounds are hydrophilic thickening agents, such as carbomers; solubilizing agents such as polymers, for example polyethylene glycol or polyvinylpyrrolidone (PVP). Polar compounds as mentioned herein may be used in combination with hydrophilic or lipophilic versions of active ingredients described in the present invention.

One embodiment involves the use of an oil (lipid) soluble active dissolved in an oily carrier, wherein the oily carrier may be present with an aqueous phase to form an emulsion. In certain embodiments, the active is dissolved in an oily carrier to form a simple solution.

An "oily carrier" as used herein refers to the compounds as are commonly known in the art to make cosmetics or dermatologic formulations, such as emulsions. Examples include naturally derived oils, waxes, or wax esters, synthetic oils, waxes, or wax esters. Silicones are also envisioned as components of the carrier, as well as glycerine compounds, polymers, co-polymers, and other common formulation ingredients in cosmetics.

Naturally derived oily carriers include but are not limited to apricot kernel oil, arachis oil, avocado oil, babassu oil, baobab oil, blackcurrant seed oil, borage oil, calendula oil, castor oil, coconut oil, cranberry seed oil, evening primrose oil, grape seed oil, hazelnut oil, hemp oil, illipe butter, jojoba oil, kukui nut oil, macadamia oil, mango butter, moringa oil, olive oil, papaya seed oil, peach kernel oil, plum oil, pomegranate seed oil, rapeseed oil, rice bran oil, rosehip oil, safflower oil, sesame oil, shea nut butter, soybean oil, strawberry seed oil, sunflower oil, sweet almond oil, and wheat germ oil.

In certain embodiments, the active, which may be an underivatized fullerene, a fullerene derivative, a fullerene-derived ketolactam is dissolved in a naturally-derived oily carrier. In certain embodiments, the carrier is grape seed oil, in a concentration between 0.001% (wt.) and 25% (wt.), between 0.01% (wt.) and 15% (wt.), or between 0.1% (wt.) and 5% (wt.). Other small amounts of compounds are normally present in such naturally derived oily carriers, such as antioxidants (e.g., polyphenolics), vitamins, fatty acids, esters, and the like and are acceptable for use in the carrier.

In certain embodiments, the active is present as a dissolved compound in a liquid oily carrier, in a concentration sufficient to impart enough color to the carrier whereby the absorbance of the formulation compared to the parent oil is increased in the range of 100% or more. This allows for less light to penetrate the solution, which serves to protect the solution from potential photo-oxidation. In such embodiments, the color imparted by the active is noticeably amber, brownish-red, brown, or gray. Underivatized fullerenes, if used to make such a formulation, may give a magenta or reddish color. Different fullerenes, fullerene derivatives, or fullerene-derived keto-lactams may require different concentrations to give a similar optical density.

It has been found that such a simple solution of a fullerene, fullerene derivative, or fullerene-derived ketolactam dissolved in an oily substance provides for a particularly effective method of applying the active to keratinous tissue, since it allows for a small amount of formulation to be applied for a given desired dosage of active, and with minimal other components which may alter or diminish the efficacy of the active, or which may give unwanted side effects when applied to the skin. In addition, such simple solutions of a fullerene-derived or fullerene active wherein the optical density has been significantly increased compared to the parent carrier offer the advantage of being more stable with respect to UV or visible light induced oxidation.

Fullerenes, upon light absorbance, produce the triplet state with varying yields depending on the fullerene and nature of chemical derivative (from about 0.1-1 quantum yield, as described above), which produces singlet oxygen in varying yields depending on the fullerene and nature of chemical derivative (from about 0.1-1 quantum yield). Generation of singlet oxygen is known to produce degradation products resulting from reaction of the singlet oxygen or other products of the fullerene triplet state (such as superoxide), for example epoxides, that have been shown to be products of reaction of singlet oxygen with the triplet excited state of the fullerene.

Reduction in the relative amount of degradation of any fullerene, fullerene derivative, or fullerene-derived ketolactam containing formula would be desired, to minimize the loss of activity of the formula via photooxidation. Even for compounds, such as those of the present invention, which have a reduced net singlet oxygen generation, may undergo photooxidation and break down, and thus it is desirable to reduce or prevent such photooxidation.

Reduction in the overall transmittance (making the formula more optically dense) is one way to accomplish a reduction in the overall percentage of the active in a formulation that may photooxidize.

Light intensity in a liquid formulation, such as a liquid oil formulation, decays along the optical path according to the Beer-Lambert law:

$$I_1/I_0 = 10^{-A}$$

Where $I_1$ is the intensity of light at a given location within the sample, $I_0$ is the initial intensity of light, and A is the absorbance. The intensity of light at a given location in the formulation correlates with the rate of photochemically activated reaction, i.e., lower intensities correspond to lower rates of photochemical reaction, all other factors being equal.

Therefore increases in the absorbance (or decreases in the transmittance) can have a dramatic effect on reducing the rate of reaction of photooxidation. This effect is used practically, for example to reduce polymer photooxidation by addition of UV absorbers to decrease photon density within a polymer.

In some cases, total photooxidation may not be prevented, but the amount of photooxidation may be reduced, allowing for example for a longer shelf-life. Shelf-live of cosmetics products is important, since in the EU each product must display a "period after opening" (PAO) date, and longer PAO dates are preferred.

Dyes or pigments (e.g., carbon black) may also be used to increase the absorption and reduce photooxidation, as is known in the art to prevent photooxidation of polymers.

It is not common for cosmetics formulations to be strongly colored in appearance, as historically, it is believed that white or only slightly colored cosmetics products are more desirable to the consumer. Thus, the minimization of photooxidation by increasing absorbance of the formulation and thus decreasing the incident light within the formulation has not been previously utilized.

It has been found that simple liquid lipid formulations wherein the formulation is visibly dark due to the presence of a fullerene, fullerene derivative, or fullerene-derived ketolactam remain stable for relatively long times (e.g., 6, 9, or 12 months or more), and this effect is believed to be at least partly due to the effect of the formulation being significantly more optically dense than the neat parent oil. For example, it is known in the art that a dilute solution of $C_{60}$ in toluene exposed to light and air will undergo approximately 10% or more degradation and loss of the $C_{60}$ due to epoxidation and subsequent breakdown of the fullerene cage resulting from singlet oxygen generated via photoexcitation of the $C_{60}$. This can be seen even visually since the decomposed $C_{60}$ forms a blackish product which settles out of solution.

Formulations of a fullerene derivative and HG2-V1 and HG2-V2 dissolved in grape seed oil which are noticeably darker than the parent oil, but which still are convenient for use on the skin (e.g., no staining of the skin is observed and the formulation is not unpleasant to use) exposed to light and air for up to a year give a reduced amount of decomposition products.

Likewise, it has been discovered that fullerenes or fullerene derivatives dissolved in a suitable solvent (e.g. aromatic) at sufficiently high concentrations to reduce the optical transmittance of the solution react with a slower rate, as a percentage of the starting fullerene or fullerene derivative concentration, when exposed to light compared to similar solutions at a lower concentration.

The formulation is therefore envisioned in which any fullerene, fullerene derivative, or fullerene-derived ketolactam is dissolved in an oily carrier oil in the range of about 0.001% (wt.) to 20% (wt.), 0.01% (wt.) to 10% (wt.), or 0.1% (wt.) to 5% (wt.), wherein the formulation is significantly more optically dense than the parent carrier. The increase of the optical density of the formulation may be accomplished by the active itself, but may optionally be accomplished by the addition of dyes, pigments, or other coloring agents. It is described below how one may determine such an optimal concentration of the dyeing agent; in certain embodiments, the dyeing agent is also the active ingredient (the fullerene, fullerene derivative or fullerene-derived ketolactam), to minimize, reduce, or eliminate the photochemically activated decomposition of the formulation.

Figure 5:
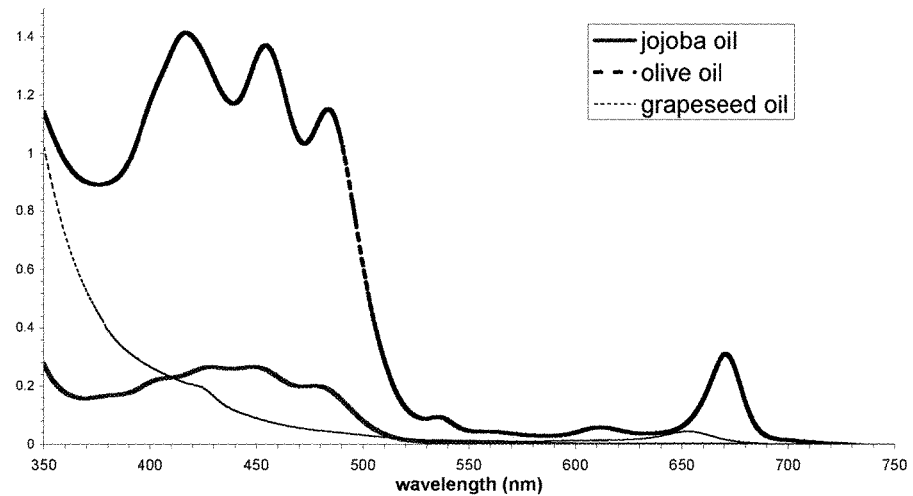
FIG. 5 depicts examples of the UV-Vis spectra (measured against water) of various commercially available oils (an olive oil, a jojoba oil, and a grapeseed oil). Both a spectrum [a] for $\lambda$=350-800 nm and an enlargement [b] for the area between $\lambda$=500 and $\lambda$=600 nm is shown.
Figure 5:
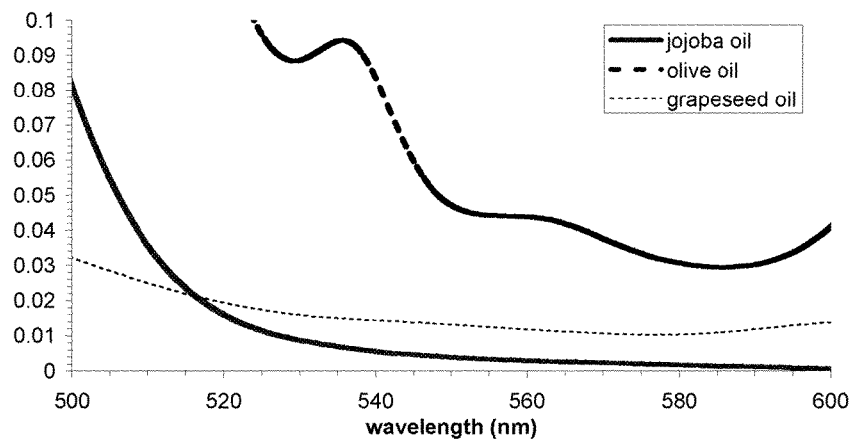

Naturally-derived oily carriers, such as grapeseed oil, olive oil, jojoba oil (technically a wax ester), or sunflower oil, which are commonly used in cosmetics formulations have a low absorbance of light at a wavelength (λ) of approximately λ=570 nm. Consequently, these oils are pale yellow, green, or yellow-green. Examples of the UV-Vis spectra (measured against water) of various commercially available oils (an olive oil, a jojoba oil, and a grapeseed oil) are shown in FIG. 5.

All of these oils show an absorbance (A) at λ=570 nm of $A_{570}$ less than 0.05 when measuring the neat oil against water, using 1 cm cuvettes as is general practice. The above absorbance profiles were measured by placing the neat oil in the 1 cm path length spectrometer cuvette. It can be seen that the oils do not absorb significantly in the visible or UV visible regions, and visually, they are relatively clear, only lightly colored solutions of a yellowish, or greenish yellow color. Olive oil typically has a darker appearance (and is thus more optically dense) than the other oils, and this can be seen in the absorption profile.

Figure 6:
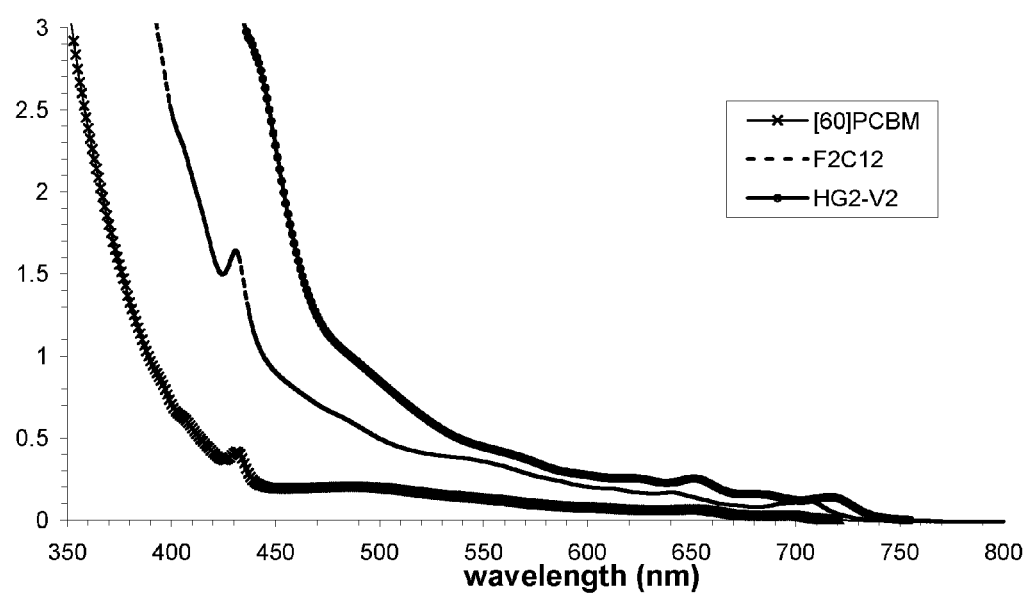
FIG. 6 depicts a spectrum (non-diluted, against $H_2O$) of a methanofullerene ([6,6]-phenyl $C_{61}$ butyric acid methyl ester, [60]PCBM, 0.82 mg/10 mL), a fulleropyrrolidine (1'-Methyl-1',5'-dihydro-2'-(3,5-didodecyloxyphenyl)-1H-pyrrolo[3',4':1,9](C60-Ih)[5,6]fullerene, F2C12, 2.11 mg/5 mL), and the ketolactam compound HG2-V2 (5.1 mg/10 mL) in grapeseed oil. See D. E Markov, et al., J. Phys. Chem. A, 109, 5266, 2005.

Spectra of various fullerene derivatives and a fullerene-derived ketolactam of the instant invention dissolved in neat grapeseed oil are depicted in FIG. 6. It is clear that invariably there is a more significant absorbance at 570 nm, even though the neat oil shows almost no absorbance at this wavelength as was shown above. The fullerene derivatives and fullerene-derived ketolactam also noticeably increase the absorption profile compared to the neat parent oil throughout the range of UV and visible wavelengths. 570 nm is chosen as a convenient wavelength at which to measure the increase of optical absorption, or "darkness" or "optical opacity" of the finished formulation.

Figure 7:
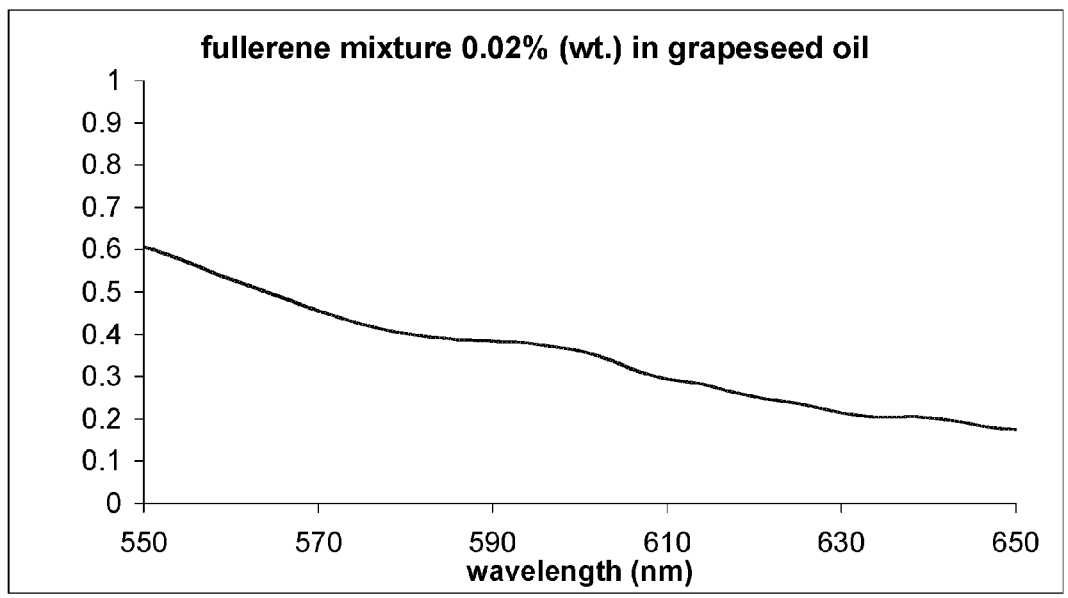
FIG. 7 depicts the absorption of a 0.02% by weight mixture of underivatized fullerenes (a mixture of $C_{60}/C_{70}$/higher fullerenes approximately in the molar proportion 70%/25%/5%) in grapeseed oil.

Un-derivatized fullerenes also may impart the desired increase in absorbance and thus allow for less photooxidation and improved shelf-life. Figure below shows underivatized fullerenes (a mixture of $C_{60}/C_{70}$/higher fullerenes approximately in the molar proportion 70%/25%/5%). It can be seen that the formulation has a significantly increased optical absorption compared to the neat parent grapeseed oil as shown FIG. 7. Visually, the formulation is noticeably darker and more optically opaque than the parent neat grapeseed oil.

Fullerenes higher in molecular weight than $C_{60}$, the "higher fullerenes," e.g., $C_{70}$, $C_{76}$, $C_{78}$, $C_{84}$, typically have significantly higher optical absorption values than $C_{60}$, and so it may be desirable in some cases to use $C_{70}$, $C_{76}$, $C_{78}$, or $C_{84}$, either alone or in mixtures, or chemical derivatives of the higher fullerenes either alone or in mixtures to increase the optical density of a formulation. Depending on which fullerene is used or if a chemical derivative is used, the relative increase in absorption compared to the neat parent oil may differ. Certain fullerenes may offer a different absorption value at the same concentration.

Figure 8:
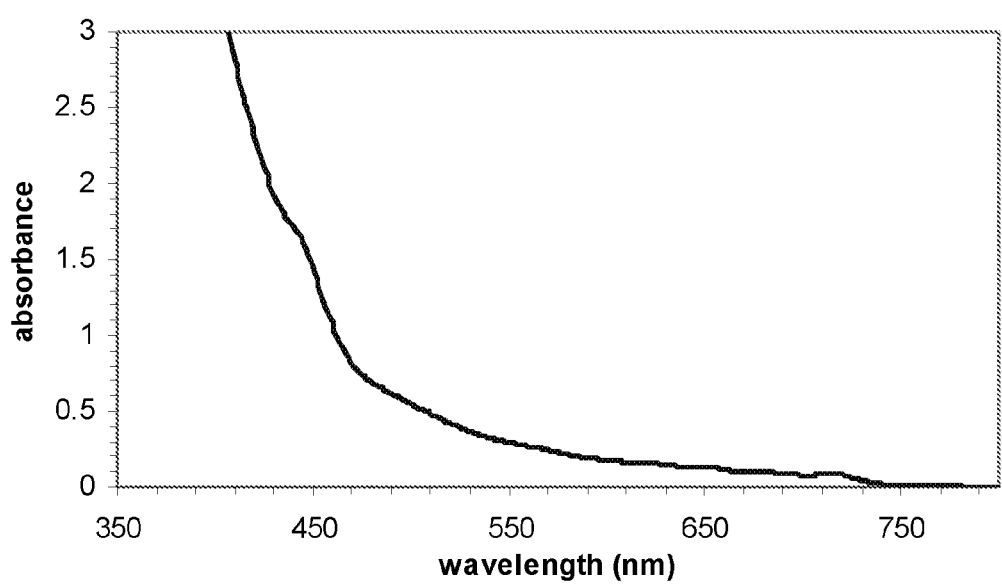
FIG. 8 depicts the spectrum of a concentrated solution of HG2-V2 in grapeseed oil (9.2 mg HG2-V2 dissolved in 3 mL), diluted ten times (v/v) with toluene.

In many instances, the concentration of fullerene, fullerene derivative, or fullerene-derived ketolactam desired due to considerations of optimal antioxidant efficacy is higher than can be conveniently measured by standard UV/vis spectroscopy. For concentrated solutions, dilution may be necessary to obtain a proper spectrum in the so-called visible area ($\lambda$=400-700 nm). If such concentrated solutions are measured without dilution, $A_{570}$ may exceed a limit to obtain an accurate measurement, or may even exceed the maximum value that can be measured by the spectrometer. As an example, the spectrum of a concentrated solution of HG2-V2 in grapeseed oil (9.2 mg HG2-V2 dissolved in 3 mL), diluted×10 (v/v) with toluene, is shown in FIG. 8. Here, $A_{570}$ is 0.24, meaning that without dilution it would give approximately A=2.4. Common UV-Vis spectrometers can usually measure up to A≈5, meaning that for this solution a large part of the spectrum ($\lambda$<510 nm) could not have been accurately measured without dilution.

Such increases in optical absorbance may also be utilized for cosmetically or dermatologically acceptable formulations which are multi-phase, such as emulsions, as described herein, by increasing the absorbance, as described herein, of the liquid component in which the fullerene, fullerene derivative, or fullerene-derived ketolactam is dissolved or suspended, for example by measurement of the absorbance of said liquid phase before addition of other liquid phases, emulsifiers, etc., for example when forming a cream or lotion.

It is taught herein that a simple formulation wherein a fullerene, fullerene derivative, or fullerene-derived ketolactam is dissolved in a liquid lipid oil gives desirable properties of formulation of a radical scavenger for skin care application, allowing for a minimal number of ingredients that may diminish the efficacy.

It is also taught herein that addition of an epoxidized version of a fullerene, fullerene derivative, or fullerene-derived ketolactam to a formulation intended for skin care application can act to preserve the formulation and/or reduce the generation of singlet oxygen and/or superoxide formed by photoexcited states of said fullerene, fullerene derivative, or fullerene derived ketolactam. This follows from the finding (see Example 3[f]) that though the quantum yield of $^1O_2$ generation of fullerenes and fullerene derivatives is high (up to 1.0), the net generation of $^1O_2$ is surprisingly low compared to well-known photosensitizers, such as methylene blue (MB), and lower than would be predicted by the singlet oxygen quantum yield and optical absorption of the fullerene, fullerene derivative, or fullerene-derived ketolactam. The $^1O_2$ quantum yield of MB is ~0.5, about half of PCBM (~1.0), however, the net generation of $^1O_2$ is 250 times higher for MB than for PCBM on an equimolar basis. The average optical absorption between 400 nm and 700 nm is about 10 times higher for MB compared to PCBM, therefore, MB produces 25 times the amount of $^1O_2$ as PCBM on an equal absorption and equimolar basis, though it has a $^1O_2$ quantum yield half that of PCBM. This demonstrates the effect that the net $^1O_2$ generation of fullerenes is in fact much lower than expected, due to the quenching effects of epoxide reaction products formed by the photooxidation, which are known to be quenchers of the photoexcited fullerene triplet state. However, the effect of fullerene epoxides on the net generation of $^1O_2$ has not been demonstrated until now. Therefore, addition of mono- and multi-epoxidized fullerenes, fullerene derivatives, or fullerene-derived ketolactams to a formulation can act to minimize the reaction products of the photoexcited states of the fullerene, fullerene derivative, or fullerene-derived ketolactam.

It is further taught herein that one skilled in the art may prolong shelf-life of the formulation by taking into account what minimum concentrations are necessary to impart increased absorbance to the formulation, as measured by the optical absorption spectra at wavelength of 570 nm, so as to reduce photooxidation and increase the shelf-life of the formulation. Therefore, it is taught herein that in cases where the active concentration is thought to be sufficient in terms of antioxidant efficacy, it may be advantageous to increase the concentration of active or add a light absorbing additive to increase the optical absorption and thus decrease the potential for photochemically activated oxidation of the formulation, and thus to provide a more stable formulation from the standpoint of shelf-life. Having such optically dense formulations allows for more packaging options, e.g., glass containers which are not amber colored, to be used, which may be desired in some cases so as to create a more appealing product. Optically dense formulations of the present invention utilizing fullerenes, fullerene derivatives, or fullerene-derived ketolactams are also surprisingly not unpleasant in use, since the darkness of the formulations does not stain the skin for a significant period of time. Further, having a more optically dense formulation may also confer advantages after application, as the film formed on the skin is resultantly also more optically dense, and thus allows for less light transmittance through the film to the portions of active which penetrate the skin.

A formulation wherein the photooxidation properties are improved may be obtained by measuring the increase in optical absorption at 570 nm as measured by placing the liquid oil formulation in a 1 cm cuvette and ensuring $A_{570}$ is 0.1 or greater, which for most oils amounts to an increase in the optical density by a factor of 2 or more compared to the neat parent oil. In certain embodiments, $A_{570}$ of the final formulation of fullerene, fullerene derivative or fullerene-derived ketolactam dissolved or suspended in an oily carrier is 0.25 or higher. In other embodiments, $A_{570}$ of the final formulation is greater than 0.5. For reference, for an oil such as grape seed oil where the absorbance at 570 nm is approximately 0.01, an increase of the absorbance to 0.1 can be calculated by Beer-Lambert's law to amount to approximately a 20% decrease in transmitted light intensity at 570 nm, and assuming first order kinetics of photoactivation, roughly a 20% decrease in the rate of photochemical oxidation, as the increase in absorbance is typically throughout the visible and UV spectrum. Similarly, an increase to absorbance of 0.5 decreases the rate of photochemical oxidation approximately 70%.

Other optional compounds which may be added to this formulation include perfume agents, such as but not limited to essential oils or synthetic additives as commonly used in the perfume industry, in the range of between 0.00001% (wt.) and 1% (wt.), or in the range of 0.0001% (wt.) to 0.001% (wt.). Such perfume agents include those as are commonly used in the art to make perfumes, such as lavender oil, and other oils derived from plant or animal sources. One such formulation includes the use of pure lavender oil obtained naturally (Product #301981, "Pure Lavender Oil" from Norfolk Lavender, Ltd., UK) in a concentration of approximately 0.0003% (wt.) added to the grapeseed oil carrier, which contains HG2-V2 for example in a concentration in the range about 0.1% (wt.) to about 0.6% (wt.). This concentration of the lavender oil imparts a barely perceptible note of lavender, and serves to mask the faint odor of the grape seed oil, without giving a noticeably strong scent. Lavender oil is one scent that may be used in the invention as it has been shown to have beneficial aromatherapeutic properties, is well tolerated by the skin, and has been shown as well to have beneficial properties in skincare, such as anti-inflammatory properties.

In addition, other lipid soluble compounds, including but not limited to antioxidants, including but not limited to Vitamin E, retinoids, polyphenolic compounds, Coenzyme Q10, or other active additives may be added to the formulation. In some cases, additives necessary for the stability and preservation of the carrier may be necessary, as described under the heading "Other Components" in the present document.

Such a formulation as described above has the advantages of providing a safe and effective amount of the active while being made of few components and with minimal use of other carrier compounds which are necessary for more complex formulations, such as emulsions. For example, anti-microbial agents are typically not necessary if an aqueous phase is not present. Likewise, emulsifiers are not necessary if the formulation is single phase. In addition the presence of a bi-phase emulsion or the presence of other compounds may alter the transport and/or affinity of the fullerene-derived ketolactams of the present invention, and so it is desirable to preserve the inherent solubility and affinity of the compounds of the present invention without any alteration in these properties that may be caused by the presence of other compounds. Thus, this skincare formulation provides for topical application of only the free radical scavengers of the present invention with the need for less other compounds which may not provide benefits or may even provide unwanted side effects. Such a formulation provides efficient delivery of the compounds of the present invention past the stratum corneum barrier, which is mainly lipophilic.

Alternatively, water soluble versions of the active may be used to form optically dense simple solutions as described above, where the carrier is aqueous or polar, such as water or alcohols, and the active is present as a suspended particulate, or dissolved in the aqueous carrier.

Other suitable carriers comprise an emulsion such as oil-in-water emulsions (e.g., silicone in water) and water-in-oil emulsions, (e.g., water-in-silicone emulsions). As will be understood by the skilled artisan, a given component will distribute primarily into either the water or oil phase, depending on the water solubility/dispensability of the component in the composition.

Emulsions according to the present invention generally contain an aqueous phase and a lipid or oil. Emulsions may further contain from about 0.1% (wt.) to about 10% (wt.), or from about 0.2% (wt.) to about 5% (wt.), of an emulsifier, based on the weight of the composition. Emulsifiers may be nonionic, anionic or cationic. Suitable emulsifiers are disclosed in, for example, McCutcheon's Detergents and Emulsifiers, North American Edition, pages 317-324 (1986). Suitable emulsions may have a wide range of viscosities, depending on the desired product form, to form what is known in the art as lotions or creams.

The acceptable carriers of the present invention may also contain a variety of other ingredients that are conventionally used in given product types provided that they do not unacceptably alter the benefits of the invention.

The optional components, when incorporated into the composition, should be suitable for use in contact with human keratinous tissue without undue toxicity, incompatibility, instability, allergic response, and the like within the scope of sound judgment. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components, such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents, skin-conditioning agents, skin soothing and/or healing agents and derivatives, skin treating agents, thickeners, and vitamins and derivatives thereof.

Formulations containing the compounds of the present invention intended for topical use in skincare may contain from 0.001% (wt.) or less to up to 20% (wt.) or more of the compound(s) of the present invention, depending on the intended use and/or specific compound.

Oxidative stress caused by free radicals from environmental sources, such as exposure to light, pollution, cigarette smoke, atmospheric ozone, etc. may be prevented or remediated through the use of the present compounds.

The compounds of the present invention may be used as agents to ameliorate immune system responses to various conditions involve the generation of free radical species, such as .NO, which is generated by the immune system to combat bacterial infection, in response to irritants, etc. For example, the red, swollen appearance of acne lesions may be reduced through the application of the present compounds.

Likewise, the inflammatory responses coincident with psoriasis, eczema, rosacea and other conditions that are the result of immune system response may be reduced.

The compounds of the present invention are also envisioned to improve the overall health and appearance of the skin, especially of the face. Improvements in overall health may be gained through reduction in wrinkles, regulation of dryness and oiliness, improvement in skin thickness, reduction of hyper-pigmentation (age spots, moles, or other discoloration), reduction of scarring caused by skin wounds, acne lesions, or other conditions leading to scarring, and other improvements in the overall healthiness of the skin.

The compounds of the present invention may be used for minimizing the effects of exposure to the sun, e.g., application after sun exposure to minimize sun-burn and peeling. The compounds of the present invention may also be used to prevent oxidative damage caused by exposure to sunlight.

The compounds of the present invention may be used where no pre-existing condition exists, to provide moisturizing benefits and/or for the prevention of free radical-related conditions, such as acne, photo-aging, etc.

The compounds of the present invention may be used to ameliorate the effects of "chemical peel" treatments, such as commonly performed using α-glycolic acids, β-glycolic acids, lactic acids, or other chemical agents, allowing for accelerated re-appearance of healthy skin, reduction in sensitivity, or other effects of chemical peel treatments.

The compounds of the present invention may be used to ameliorate the effects of laser treatments of the skin, such as commonly performed for reduction in wrinkles, removal of tattoos, removal of abnormal growths, removal of hyper-pigmentation or other uses, allowing for accelerated re-appearance of healthy skin, reduction in sensitivity, or other effects of laser treatments.

The compounds of the present invention may be used to accelerate healing of wounds to the skin.

The compounds of the present invention may be used to prevent, ameliorate, or remediate abnormal skin growths, such as non-cancerous or cancerous growths, such as melanoma, warts, or cysts.

In general, any condition where free radicals lead to damage or other detriment to the skin may be ameliorated through use of the present compounds, such as erythema caused by radiation treatment or chemotherapy, sun-burn and peeling, chemical or thermal burns, inflammatory disorders, photo-aging, wrinkling, loss of skin thickness, extrinsic aging leading to sagging of the skin, sallow color, etc.

The present compounds are also envisioned to accelerate the natural healing of such conditions, such as but not limited to: damage to the skin caused by inflammatory responses, such as acne, psoriasis, eczema, skin wounds, laser treatment, chemical peels, radiation treatment, chemotherapy, thermal burns, or other unhealthy conditions of the skin.

The present compounds are envisioned to be used as a component in or additive to sun screen or sun-block formulations to prevent or ameliorate the effects of sun exposure, such as erythema.

The compounds of the present invention may also be used either alone or in conjunction with other nutritional or pharmaceutical ingredients in formulations which are well known in the art, such as drug-delivery agents, excipient agents, etc. for oral, intravenous, sub-lingual, intra-muscular or other dosing methods in humans or animals for the prevention or amelioration of conditions, such as deteriorating neurological conditions, such as Parkinson's disease, Alzheimer's disease, or other neurological conditions where ROS are implicated as causative or exacerbating agents. In addition, the compounds of the present invention may be used to ameliorate or prevent atherosclerosis, increase general health, increase life-span, or for other conditions where antioxidants are used or prescribed.

The compounds of the present invention may be used as radical scavenging agents in non-biological applications where radical scavenging is desired, such as food preservatives, polymer preservatives, personal care formulation preservatives, or other applications where antioxidants are commonly used.

In addition, the fullerene-derived ketolactam derivatives exhibit lower LUMO levels than the parent fullerene, which may be desirable in various organic electronics applications for us as an n-type or ambipolar semiconductor. Organic electronics applications include but are not limited to organic photodiodes (photovoltaics, photodetectors), or organic transistors. The lower LUMO levels of the fullerene-derived ketolactam compared to the parent fullerene may be particularly applicable for use as an n-type or ambipolar semiconductor in organic transistor applications.

Definitions

For convenience, certain terms employed in the specification, examples, and appended claims are collected here.

The term "adduct" is art-recognized and refers to a new molecular species (AB) formed by direct combination of two separate molecular entities (A+B). The term "bis-adduct" refers to molecular species $AB_2$. The term "tris-adduct" refers to molecular species $AB_3$. The terms "adduct" and "derivative" are used interchangeably herein. In certain embodiments, species A represents the fullerene core and species B an addend.

The term "addend" refers to a chemical which is bonded to the fullerene core. For example, the phenyl-pentanoic-acid-methyl-ester moiety of PCBM is referred to as an addend moiety.

Figure 1:
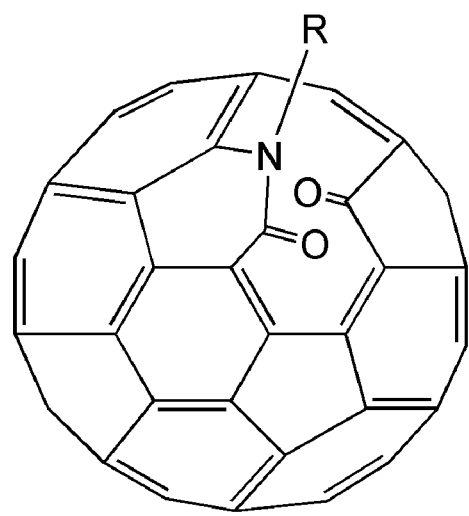
FIG. 1 depicts a fullerene-derived ketolactam (Molecule 1).

The term "fullerene-derived ketolactam" refers to a chemical with the structure of Molecule 1 (FIG. 1), where R can be any chemical group. Said fullerene-derived ketolactams may be further altered by the modification of the fullerene cage to include one or more additional ketolactam moieties, and/or the addition of one or more chemical addends, as described above.

The term "animal" as used herein may mean fish, amphibians, reptiles, birds, and mammals, such as mice, rats, rabbits, goats, cats, dogs, cows, and apes.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams, such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" is art-recognized and refers to an aromatic or non-aromatic ring in which each atom of the ring is carbon.

The term "nitro" is art-recognized and refers to —NO$_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

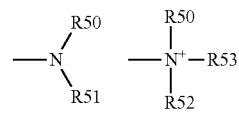

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

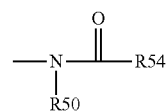

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

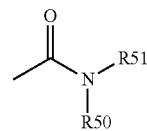

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S— alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

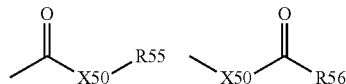

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

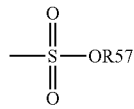

in which R57 is an electron pair, hydrogen, alkyl, cycloalkyl, or aryl.

The term "sulfate" is art recognized and includes a moiety that may be represented by the general formula:

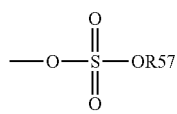

in which R57 is as defined above.

The term "sulfonamido" is art recognized and includes a moiety that may be represented by the general formula:

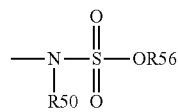

in which R50 and R56 are as defined above.

The term "sulfamoyl" is art-recognized and refers to a moiety that may be represented by the general formula:

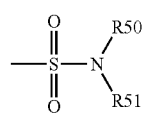

in which R50 and R51 are as defined above.

The term "sulfonyl" is art-recognized and refers to a moiety that may be represented by the general formula:

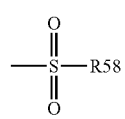

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

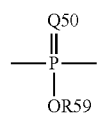

wherein Q50 represents S or O, and R59 represents hydrogen, a lower alkyl or an aryl. When used to substitute, e.g., an alkyl, the phosphoryl group of the phosphorylalkyl may be represented by the general formulas:

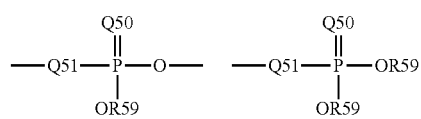

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

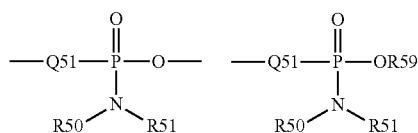

wherein Q51, R50, R51 and R59 are as defined above.

The term "phosphonamidite" is art-recognized and may be represented in the general formulas:

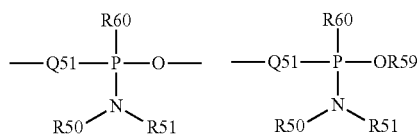

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g., alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms, such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

Certain Compositions and Uses of the Invention

Formula I

One aspect of the present invention relates to a fullerene-derived ketolactam selected from the group consisting of $C_{60}$-derived ketolactam compounds of formula I:

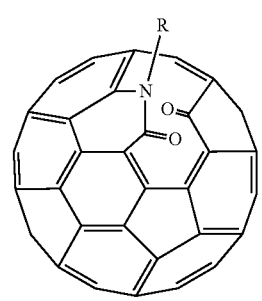

I or compounds of formula I wherein one or more additional addends are bonded to the fullerene cage, and the corresponding $C_{70}$, $C_{76}$, $C_{78}$, $C_{84}$, or $C_{90}$ analogs thereof, wherein R is a $C_1$-$C_{30}$ alkyl, $C_1$-$C_{30}$ alkenyl, or $C_1$-$C_{30}$ alkynyl, said alkyl, alkenyl or alkynyl being optionally substituted with a $C_1$-$C_{20}$ alkyl group, aryl group, heteroaryl group, halogen atom, or hydroxyl group, said aryl or heteroaryl being optionally substituted with a halogen atom, hydroxyl group, $C_1$-$C_{30}$ alkyl group, $C_1$-$C_{30}$ linear alkoxy group, or a —O(CH$_2$CH$_2$O)$_n$R' group; n is 1 to 100 inclusive, and R' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

Another aspect of the present invention relates to a fullerene-derived ketolactam selected from the group consisting of $C_{60}$-derived ketolactam compounds of formula I:

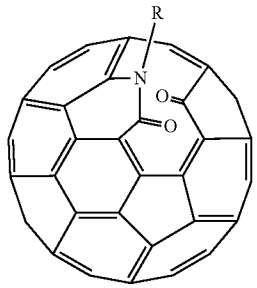

I or compounds of formula I wherein one or more additional addends are bonded to the fullerene cage, and the corresponding $C_{70}$, $C_{76}$, $C_{78}$, $C_{84}$, or $C_{90}$ analogs thereof, wherein R is a $C_1$-$C_{30}$ alkyl, $C_1$-$C_{30}$ alkenyl, or $C_1$-$C_{30}$ alkynyl, said alkyl, alkenyl or alkynyl being optionally substituted with a $C_1$-$C_{20}$ alkyl group, aryl group, heteroaryl group, halogen atom, or hydroxyl group, said aryl or heteroaryl being optionally substituted with two or more groups independently selected from the group consisting of halogen atoms, hydroxyl groups, $C_1$-$C_{30}$ alkyl groups, $C_1$-$C_{30}$ alkoxy groups, and O(CH$_2$CH$_2$O)$_n$R' groups; n is 1 to 100 inclusive, and R' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

Another aspect of the present invention relates to a fullerene-derived ketolactam selected from the group consisting of $C_{60}$-derived ketolactam compounds of formula I:

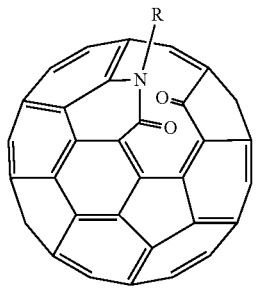

I or compounds of formula I wherein one or more additional addends are bonded to the fullerene cage, and the corresponding $C_{70}$, $C_{76}$, C78, $C_{84}$, or $C_{90}$ analogs thereof, wherein R is a $C_1$-$C_{30}$ alkyl, alkenyl, or alkynyl, said alkyl, alkenyl or alkynyl being optionally substituted with two or more groups independently selected from the group consisting of $C_1$-$C_{20}$ alkyl groups, aryls, heteroaryls, halogens, and hydroxyl groups, said aryl or heteroaryl being optionally substituted with one or more groups independently selected from the group consisting of halogen atoms, hydroxyl groups, $C_1$-$C_{30}$ alkyl groups, $C_1$-$C_{30}$ alkoxy groups, and O(CH$_2$CH$_2$O)$_n$R' groups; n is 1 to 100 inclusive; and R' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

Another aspect of the present invention relates to a fullerene-derived ketolactam selected from the group consisting of $C_{60}$-derived ketolactam compounds of formula I:

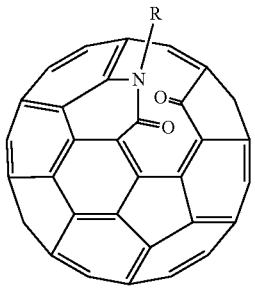

I or compounds of formula I wherein one or more additional addends are bonded to the fullerene cage, and the corresponding $C_{70}$, $C_{76}$, $C_{78}$, $C_{84}$, or $C_{90}$ analogs thereof, wherein R is aryl or heteroaryl, said aryl or heteroaryl being optionally substituted with one or more groups independently selected from the group consisting of halogen atoms, hydroxyl groups, $C_1$-$C_{30}$ alkyl groups, $C_1$-$C_{30}$ alkoxy groups, and O(CH$_2$CH$_2$O)$_n$R' groups; n is 1 to 100 inclusive; and R' is hydrogen, aryl, $C_1$-$C_{30}$ alkyl, $C_1$-$C_{30}$ alkenyl, or $C_1$-$C_{30}$ alkynyl. In certain embodiments, R may be a $C_9$-$C_{50}$ branched alkoxy group.

In certain embodiments, R is a $C_1$-$C_{50}$ alkyl, $C_1$-$C_{50}$ alkenyl, or $C_1$-$C_{50}$ alkynyl, said alkyl, alkenyl or alkynyl being optionally substituted with a $C_1$-$C_{50}$ alkyl group, aryl group, heteroaryl group, halogen atom, or hydroxyl group, said aryl or heteroaryl being optionally substituted with a halogen atom, hydroxy group, $C_1$-$C_{50}$ alkyl group, $C_1$-$C_{50}$ linear alkoxy group, or a —O(CH$_2$CH$_2$O)$_n$R' group; n is 1 to 100 inclusive; and R' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

In certain other embodiments, R is a $C_1$-$C_{50}$ alkyl, $C_1$-$C_{50}$ alkenyl, or $C_1$-$C_{50}$ alkynyl, said alkyl, alkenyl or alkynyl being optionally substituted with a $C_1$-$C_{50}$ alkyl group, aryl group, heteroaryl group, halogen atom, or hydroxyl group, said aryl or heteroaryl being optionally substituted with two or more groups independently selected from the group consisting of halogen atoms, hydroxy groups, $C_1$-$C_{50}$ alkyl groups, $C_1$-$C_{50}$ alkoxy groups, and O(CH$_2$CH$_2$O)$_n$R' groups; n is 1 to 100 inclusive; and R' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

In still other embodiments, R is a $C_1$-$C_{50}$ alkyl, alkenyl, or alkynyl, said alkyl, alkenyl or alkynyl being optionally substituted with two or more groups independently selected from the group consisting of $C_1$-$C_{50}$ alkyl groups, aryls, heteroaryls, halogens, and hydroxyl groups, said aryl or heteroaryl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_nR'$ groups; n is 1 to 100 inclusive; and R' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

In yet other embodiments, R is aryl or heteroaryl, said aryl or heteroaryl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_nR'$ groups; n is 1 to 100 inclusive; and R' is hydrogen, aryl, $C_1$-$C_{50}$ alkyl, $C_1$-$C_{50}$ alkenyl, or $C_1$-$C_{50}$ alkynyl. In certain embodiments, R may be a $C_9$-$C_{50}$ branched alkoxy group.

Formula II

One aspect of the present invention relates to a fullerene-derived ketolactam selected from the group consisting of $C_{60}$-derived ketolactam compounds of formula II:

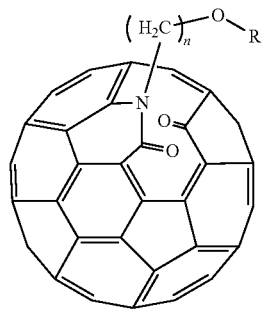

II or compounds of formula II wherein one or more additional addends are bonded to the fullerene cage, and the corresponding $C_{70}$, $C_{76}$, $C_{78}$, $C_{84}$, or $C_{90}$ analogs thereof, wherein n is 2 to 30 inclusive; R is selected from the group consisting of H, $C_1$-$C_{30}$ alkyl, $C_1$-$C_{30}$ alkenyl, $C_1$-$C_{30}$ alkynyl, aryl, and heteroaryl, said alkyl, alkenyl, alkynyl, aryl or heteroaryl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_nR'$ groups; n is 1 to 100 inclusive; and R' is H or aryl or $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

In certain embodiments, n is 2 to 30 inclusive; R is selected from the group consisting of H, $C_1$-$C_{50}$ alkyl, $C_1$-$C_{50}$ alkenyl, $C_1$-$C_{50}$ alkynyl, aryl, and heteroaryl, said alkyl, alkenyl, alkynyl, aryl or heteroaryl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_nR'$ groups; n is 1 to 100 inclusive; and R' is H or aryl or $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

Formula III

Another aspect of the present invention relates to a fullerene-derived ketolactam selected from the group consisting of $C_{60}$-derived ketolactam compounds of formula III:

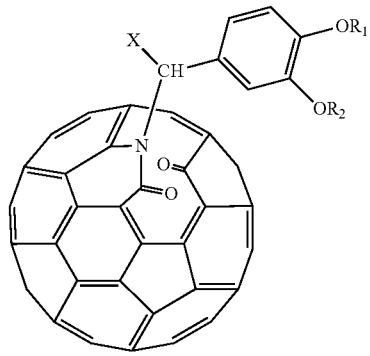

III or compounds of formula III wherein one or more additional addends are bonded to the fullerene cage, and the corresponding $C_{70}$, $C_{76}$, $C_{78}$, $C_{84}$, or $C_{90}$ analogs thereof, wherein X is selected from the group consisting of H, $C_1$-$C_{30}$ alkyl, $C_1$-$C_{30}$ alkenyl, $C_1$-$C_{30}$ alkynyl, aryl, and heteroaryl, said alkyl, alkenyl, alkynyl, aryl, or heteroaryl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_nR'$ groups; n is 1 to 100 inclusive; R' is H or aryl or $C_1$-$C_{30}$ alkyl, $C_1$-$C_{30}$ alkenyl or $C_1$-$C_{30}$ alkynyl; $R_1$ is selected from the group consisting of H, $C_1$-$C_{30}$ alkyl, $C_1$-$C_{30}$ alkenyl and $C_1$-$C_{30}$ alkynyl, said alkyl, alkenyl, or alkynyl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_mR''$ groups; m is 1 to 100 inclusive; R'' is H or aryl or $C_1$-$C_{30}$ alkyl, $C_1$-$C_{30}$ alkenyl or $C_1$-$C_{30}$ alkynyl; $R_2$ is selected from the group consisting of H, $C_1$-$C_{30}$ alkyl, $C_1$-$C_{30}$ alkenyl and $C_1$-$C_{30}$ alkynyl, said alkyl, alkenyl, or alkynyl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_pR'''$ groups; p is 1 to 100 inclusive; and R''' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

In certain embodiments, the present invention relates to the aforementioned fullerene-derived ketolactam, wherein X is H or alkyl; $R_1$ is $C_{10}$-$C_{24}$ alkyl; and $R_2$ is $CH_3$.

In certain embodiments, the present invention relates to the aforementioned fullerene-derived ketolactam, wherein X is H; $R_1$ is a $C_{22}$ alkyl; and $R_2$ is $CH_3$.

In certain embodiments, the present invention relates to the aforementioned fullerene-derived ketolactam, wherein X is H; $R_1$ is a $C_{16}$ alkyl; and $R_2$ is $CH_3$.

In certain embodiments, X is selected from the group consisting of H, $C_1$-$C_{50}$ alkyl, $C_1$-$C_{50}$ alkenyl, $C_1$-$C_{50}$ alkynyl, aryl, and heteroaryl, said alkyl, alkenyl, alkynyl, aryl, or heteroaryl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_nR'$ groups; n is 1 to 100 inclusive; R' is H or aryl or $C_1$-$C_{50}$ alkyl, $C_1$-$C_{50}$ alkenyl or $C_1$-$C_{50}$ alkynyl; $R_1$ is selected from the group consisting of H, $C_1$-$C_{50}$ alkyl, $C_1$-$C_{50}$ alkenyl and $C_1$-$C_{50}$ alkynyl, said alkyl, alkenyl, or alkynyl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_mR''$ groups; m is 1 to 100 inclusive; R'' is H or aryl or $C_1$-$C_{50}$ alkyl, $C_1$-$C_{50}$ alkenyl or $C_1$-$C_{50}$ alkynyl; $R_2$ is selected from the group consisting of H, $C_1$-$C_{50}$ alkyl, $C_1$-$C_{50}$ alkenyl and $C_1$-$C_{50}$ alkynyl, said alkyl, alkenyl, or alkynyl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_pR'''$ groups; p is 1 to 100 inclusive; and R''' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

In other embodiments, X is H or alkyl; $R_1$ is $C_{10}$-$C_{24}$ alkyl; and $R_2$ is $CH_3$.

In still other embodiments, X is H; $R_1$ is a $C_{22}$ alkyl; and $R_2$ is $CH_3$.

In yet other embodiments, X is H; $R_1$ is a $C_{16}$ alkyl; and $R_2$ is $CH_3$.

Formula IV

Another aspect of the present invention relates to a fullerene-derived ketolactam selected from the group consisting of $C_{60}$-derived ketolactam compounds of formula IV:

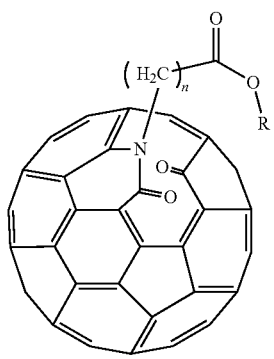

IV or compounds of formula IV wherein one or more additional addends are bonded to the fullerene cage, and the corresponding $C_{70}$, $C_{76}$, $C_{78}$, $C_{84}$, or $C_{90}$ analogs thereof, wherein n is 1 to 30 inclusive; R is selected from the group consisting of $C_1$-$C_{30}$ alkyl, $C_1$-$C_{30}$ alkenyl, $C_1$-$C_{30}$ alkynyl, aryl, and heteroaryl, said alkyl, alkenyl, aryl, heteroaryl, or alkynyl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_mR'$ groups; m is 1 to 100 inclusive; and R' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

In certain embodiments, n is 1 to 30 inclusive; R is selected from the group consisting of $C_1$-$C_{50}$ alkyl, $C_1$-$C_{50}$ alkenyl, $C_1$-$C_{50}$ alkynyl, aryl, and heteroaryl, said alkyl, alkenyl, aryl, heteroaryl, or alkynyl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_mR'$ groups; m is 1 to 100 inclusive; and R' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

Formula V

Another aspect of the present invention relates to a fullerene-derived ketolactam selected from the group consisting of $C_{60}$-derived ketolactam compounds of formula V:

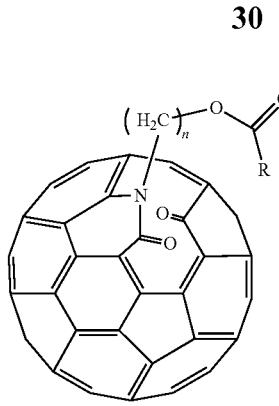

V or compounds of formula V wherein one or more additional addends are bonded to the fullerene cage, and the corresponding $C_{70}$, $C_{76}$, $C_{78}$, $C_{84}$, or $C_{90}$ analogs thereof, wherein n is 2 to 30 inclusive; R is selected from the group consisting of H, $C_1$-$C_{30}$ alkyl, $C_1$-$C_{30}$ alkenyl, $C_1$-$C_{30}$ alkynyl, aryl, and heteroaryl, said alkyl, alkenyl, aryl, heteroaryl, or alkynyl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_mR'$ groups; m is 1 to 100 inclusive; and R' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

In certain embodiments, n is 2 to 30 inclusive; R is selected from the group consisting of H, $C_1$-$C_{50}$ alkyl, $C_1$-$C_{50}$ alkenyl, $C_1$-$C_{50}$ alkynyl, aryl, and heteroaryl, said alkyl, alkenyl, aryl, heteroaryl, or alkynyl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_mR'$ groups; m is 1 to 100 inclusive; and R' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

Formula VI

Another aspect of the present invention relates to a fullerene-derived ketolactam selected from the group consisting of $C_{60}$-derived ketolactam compounds of formula VI:

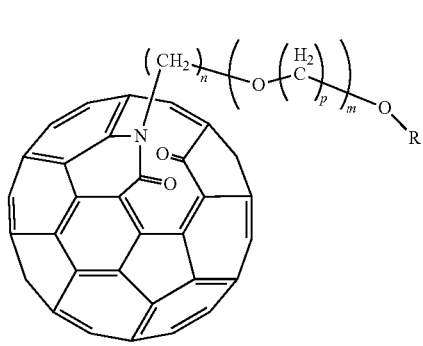

VI or compounds of formula V wherein one or more additional addends are bonded to the fullerene cage, and the corresponding $C_{70}$, $C_{76}$, $C_{78}$, $C_{84}$, or $C_{90}$ analogs thereof, wherein n is 2 to 30 inclusive; m is 1 to 100 inclusive; p is 2 or 3; R is independently selected from the group consisting of H, $C_1$-$C_{30}$ alkyl, $C_1$-$C_{30}$ alkenyl, $C_1$-$C_{30}$ alkynyl, aryl, and heteroaryl, said alkyl, alkenyl, aryl, heteroaryl, or alkynyl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_qR'$ groups; q is 1 to 100 inclusive; and R' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

Another aspect of the present invention relates to a fullerene-derived ketolactam selected from the group consisting of $C_{60}$-derived ketolactam compounds of formula VI:

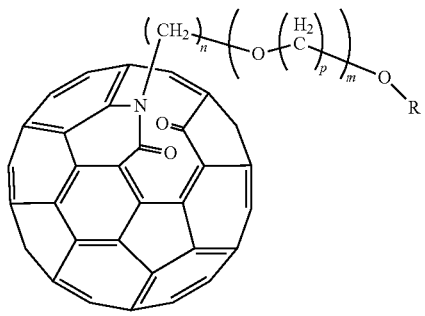

VI or compounds of formula VI wherein one or more additional addends are bonded to the fullerene cage, and the corresponding $C_{70}$, $C_{76}$, $C_{78}$, $C_{84}$, or $C_{90}$ analogs thereof, wherein n is 2 to 30 inclusive; m is 1 to 100 inclusive; p is 2 or 3; R is —C(O)—X; X is selected from the group consisting of H, $C_1$-$C_{30}$ alkyl, $C_1$-$C_{30}$ alkenyl, $C_1$-$C_{30}$ alkynyl, aryl, and heteroaryl, said alkyl, alkenyl, alkynyl, aryl, or heteroaryl being optionally substituted with one or more groups independently selected from the group consisting of halogen atoms, hydroxyl groups, $C_1$-$C_{30}$ alkyl groups, $C_1$-$C_{30}$ alkoxy groups, and $O(CH_2CH_2O)_qR'$ groups; q is 1 to 100 inclusive; and R' is hydrogen, aryl, $C_1$-$C_{30}$ alkyl, $C_1$-$C_{30}$ alkenyl or $C_1$-$C_{30}$ alkynyl. In certain embodiments, R may be a $C_9$-$C_{50}$ branched alkoxy group.

In certain embodiments, the present invention relates to the aforementioned fullerene-derived ketolactam, wherein the compound is based on $C_{60}$. In certain embodiments, the present invention relates to the aforementioned fullerene-derived ketolactam, wherein the compound is based on $C_{70}$. In certain embodiments, the present invention relates to the aforementioned fullerene-derived ketolactam, wherein the compound is based on $C_{76}$. In certain embodiments, the present invention relates to the aforementioned fullerene-derived ketolactam, wherein the compound is based on $C_{78}$. In certain embodiments, the present invention relates to the aforementioned fullerene-derived ketolactam, wherein the compound is based on $C_{84}$. In certain embodiments, the present invention relates to the aforementioned fullerene-derived ketolactam, wherein the compound is based on $C_{90}$.

In other embodiments, n is 2 to 30 inclusive; m is 1 to 100 inclusive; p is 2 or 3; R is independently selected from the group consisting of H, $C_1$-$C_{50}$ alkyl, $C_1$-$C_{50}$ alkenyl, $C_1$-$C_{50}$ alkynyl, aryl, and heteroaryl, said alkyl, alkenyl, aryl, heteroaryl, or alkynyl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_qR'$ groups; q is 1 to 100 inclusive; and R' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

In certain other embodiments, n is 2 to 30 inclusive; m is 1 to 100 inclusive; p is 2 or 3; R is —C(O)—X; X is selected from the group consisting of H, $C_1$-$C_{50}$ alkyl, $C_1$-$C_{50}$ alkenyl, $C_1$-$C_{50}$ alkynyl, aryl, and heteroaryl, said alkyl, alkenyl, alkynyl, aryl, or heteroaryl being optionally substituted with one or more groups independently selected from the group consisting of halogen atoms, hydroxy groups, $C_1$-$C_{50}$ alkyl groups, $C_1$-$C_{50}$ alkoxy groups, and $O(CH_2CH_2O)_qR'$ groups; q is 1 to 100 inclusive; and R' is hydrogen, aryl, $C_1$-$C_{50}$ alkyl, $C_1$-$C_{50}$ alkenyl or $C_1$-$C_{50}$ alkynyl. In certain embodiments, R may be a $C_9$-$C_{50}$ branched alkoxy group.

Other Fullerene Derivatives

In certain embodiments, the present invention relates to the aforementioned fullerene-derived ketolactam, wherein one or more additional addends are bonded to the fullerene cage. In certain embodiments, the present invention relates to the aforementioned fullerene-derived ketolactam, wherein said additional addends are methano-bridges, pyrrolidines, epoxides, or a mixture thereof.

In certain embodiments, the present invention relates to the aforementioned methano-bridge adducts (also referred to as methanofullerene derivatives). An example of a methanofullerene derivative is a methanofullerene having the general structure:

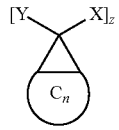

The —C(X)(Y)— group is bonded to the fullerene via a methano-bridge, which may be obtained through the well-known diazoalkane addition chemistry (W. Andreoni (ed.), *The Chemical Physics of Fullerenes* 10 (*and* 5) *Years Later,* 257-265, Kluwer, 1996.). X and Y are aryl, alkyl, or other chemical moieties which can be suitably bonded via the diazoalkane addition either by modification of the diazoalkane precursor or after the diazoalkane addition by modification of the fullerene derivative. In the mono-adduct derivative z is 1; in the bis-adduct derivative, z is 2, and so on.

One example is the molecule where X is an un-substituted aryl, and Y is butyric-acid-methyl-ester. This molecule is commonly termed phenyl-$C_n$-butyric-acid-methyl-ester (PCBM):

[$C_n$]PCBM

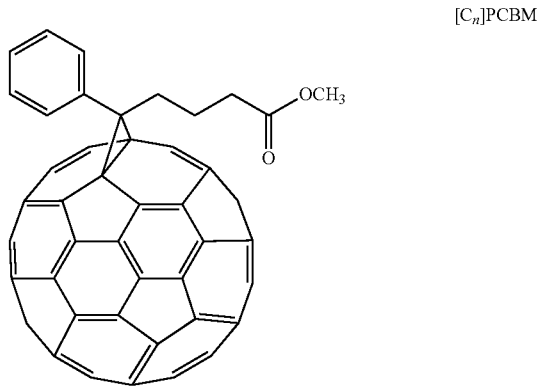 [SMILES: COC(=O)CCCC1(c2ccccc2)C23C=Cc4cc5c6c7c4C21c1c2c4c(cc8ccc9cc(c6c6c9c8c4c6c17)C5)CC2=C3]

Another example is the molecule where X is a thiophenyl, and Y is butyric-acid-methyl-ester. This molecule is commonly termed thienyl-$C_n$-butyric-acid-methyl-ester ([$C_n$] ThCBM):

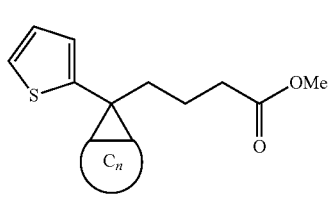

[C$_n$]ThCBM

In the two examples above, n represents the number of carbons comprising the fullerene and is 60, 70, 76, 78, 84, 90, or greater.

In certain embodiments, the present invention relates to the aforementioned pyrrolidine fullerene derivatives. One example is the Prato fullerene derivative, represented by the general structure:

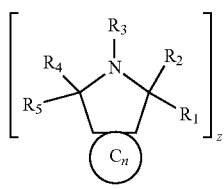

wherein $C_n$ is a fullerene bonded to —C(R$_4$R$_5$)—N(R$_3$)—C(R$_1$R$_2$)—;

n is 60, 70, 76, 78, 84, 90, or greater;

R$_1$ is optionally substituted aryl or aralkyl;

R$_2$, R$_3$, R$_4$, and R$_5$ are independently optionally substituted alkyl, optionally substituted cycloalkyl, optionally substituted heteroalkyl, optionally substituted heterocycloalkyl, optionally substituted alkenyl, or optionally substituted aralkyl; and z is 1 to 6.

In certain embodiments, the present invention relates to the aforementioned epoxides, wherein a fullerene, fullerene derivative, or fullerene-derived ketolactam has one or more epoxides bonded to the fullerene cage or fullerene-derived ketolactam, as depicted in the structures below. Such derivatives may be used in formulations as a sole ingredient, or as an additive to formulations comprising one or more fullerenes, fullerene derivatives, or fullerene-derived ketolactams as actives. The fullerene, fullerene derivative or fullerene-derived ketolactam to which one or more epoxides are bonded may be C$_{60}$, C$_{70}$, C$_{76}$, C$_{78}$, C$_{84}$, or C$_{90}$ and m may be about 1 to about 20. Such epoxides act to quench the photoexcited states of a fullerene, fullerene derivative, or fullerene-derived ketolactam, and thus may be used as an additive in the range of 0.001% (wt.) to 20% (wt.) to a formulation, for example useful in skin care, comprising one or more fullerenes, fullerene derivatives, or fullerene-derived ketolactams. One or more of the epoxides described herein may also be used as an antioxidant active alone, in the range of 0.001% (wt.) to 20% (wt.), 0.01% (wt.) to 10% (wt.), 0.1% (wt.) to 0.5% (wt.) in a skin care formulation as described herein. Without intending to be limiting, examples of epoxides bonded to the cage of a fullerene, fullerene-derived ketolactam, and fullerene derivatives are depicted below.

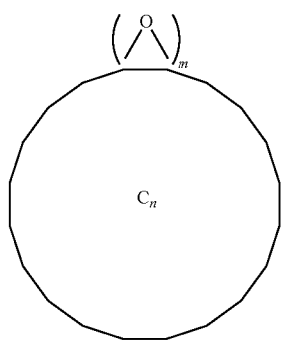

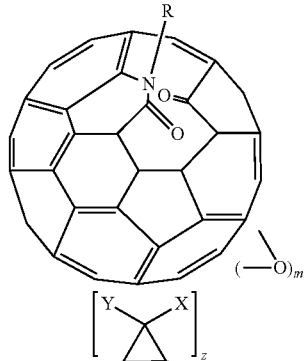

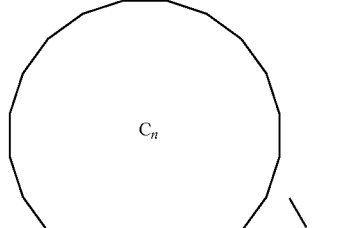

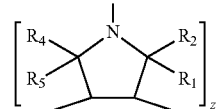

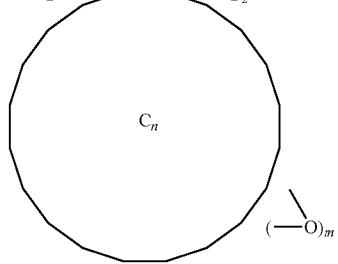

Another aspect of the present invention relates to a cosmetic or dermatological composition comprising: at least one fullerene-derived ketolactam selected from the aforementioned fullerene-derived ketolactams (i.e., C$_{60}$-derived ketolactam compounds of formulas I-VI, compounds of formula I-VI wherein one or more additional adducts are bonded to the fullerene cage, and the corresponding C$_{70}$, C$_{76}$, C$_{78}$, C$_{84}$, or C$_{90}$ analogs thereof); and a cosmetically or dermatologically acceptable carrier.

In certain embodiments, the present invention relates to the aforementioned cosmetic or dermatological composition, further comprising one or more components selected from the group consisting of abrasives, absorbents, aesthetic components, such as fragrances, pigments, colorings, essential oils, skin sensates, astringents, clove oil, menthol, camphor, eucalyptus oil, eugenol, menthyl lactate, witch hazel distillate, anti-acne agents, anti-caking agents, antifoaming agents, antimicrobial agents, iodopropyl butylcarbamate, antioxidants, binders, biological additives, buffering agents, bulking agents, chelating agents, chemical additives, colorants, cosmetic astringents, cosmetic biocides, denaturants, drug astringents, external analgesics, film formers or materials, polymers for aiding the film-forming properties and substantivity of the composition, copolymer of eicosene and vinyl pyrrolidone, opacifying agents, pH adjusters, propellants, reducing agents, sequestrants, skin bleaching and lightening agents, skin-conditioning agents, skin soothing agents or derivatives, healing agents and derivatives, skin treating agents, thickeners, vitamins, and derivatives thereof.

In certain embodiments, the present invention relates to the aforementioned cosmetic or dermatological composition, further comprising lavender oil.

In certain embodiments, the present invention relates to the aforementioned cosmetic or dermatological composition, wherein the concentration of said lavender oil in said composition is between about 0.00001% (wt.) and about 0.001% (wt.).

In certain embodiments, the present invention relates to the aforementioned cosmetic or dermatological composition, further comprising at least two fullerene-derived ketolactams selected from the aforementioned fullerene-derived ketolactams (i.e., $C_{60}$-derived ketolactam compounds of formulas I-VI, compounds of formula I-VI wherein one or more additional adducts are bonded to the fullerene cage, and the corresponding $C_{70}$, $C_{76}$, $C_{78}$, $C_{84}$, or $C_{90}$ analogs thereof).

In certain embodiments, the present invention relates to the aforementioned cosmetic or dermatological composition, wherein the cosmetic or dermatologically acceptable carrier is selected from the group consisting of natural oils, synthetic oils, waxes, and wax-esters.

In certain embodiments, the present invention relates to the aforementioned cosmetic or dermatological composition, wherein the composition has an absorbance value at wavelength 570 nm of greater than about 0.1.

In certain embodiments, the present invention relates to the aforementioned cosmetic or dermatological composition, wherein the composition has an absorbance value at wavelength 570 nm of greater than about 0.25.

In certain embodiments, the present invention relates to the aforementioned cosmetic or dermatological composition, wherein the composition has an absorbance value at wavelength 570 nm of greater than about 0.5.

In certain embodiments, the present invention relates to the aforementioned cosmetic or dermatological composition, wherein the cosmetic or dermatologically acceptable carrier is an emulsion selected from the group consisting of oil-in-water emulsions, water-in-oil emulsions, water-in-oil-in-water emulsions, and oil-in-water-in-silicone emulsions.

In certain embodiments, the present invention relates to the aforementioned cosmetic or dermatological composition, wherein the cosmetic or dermatologically acceptable carrier is a single, liquid phase.

In certain embodiments, the present invention relates to the aforementioned cosmetic or dermatological composition, wherein the cosmetic or dermatologically acceptable carrier is a single-phase, liquid, oily carrier.

In certain embodiments, the present invention relates to the aforementioned cosmetic or dermatological composition, wherein the cosmetic or dermatologically acceptable carrier is derived from plants.

In certain embodiments, the present invention relates to the aforementioned cosmetic or dermatological composition, wherein the cosmetic or dermatologically acceptable carrier is grape seed oil.

In certain embodiments, the present invention relates to the aforementioned cosmetic or dermatological composition, wherein said fullerene-derived ketolactam is dissolved in the cosmetic or dermatologically acceptable carrier.

In certain embodiments, the present invention relates to the aforementioned cosmetic or dermatological composition, wherein the concentration of said fullerene-derived ketolactam in said composition is between about 0.001% (wt.) and about 20% (wt.).

In certain embodiments, the present invention relates to the aforementioned cosmetic or dermatological composition, wherein the concentration of said fullerene-derived ketolactam in said composition is between about 0.01% (wt.) and about 10% (wt.).

In certain embodiments, the present invention relates to the aforementioned cosmetic or dermatological composition, wherein the concentration of said fullerene-derived ketolactam in said composition is between about 0.1% (wt.) and about 1% (wt.).

Another aspect of the present invention relates to the use of an aforementioned fullerene-derived ketolactam (i.e., $C_{60}$-derived ketolactam compounds of formulas I-VI, compounds of formula I-VI wherein one or more additional addends are bonded to the fullerene cage, and the corresponding $C_{70}$, $C_{76}$, $C_{78}$, $C_{84}$, or $C_{90}$ analogs thereof) to scavenge free radicals.

Another aspect of the present invention relates to the use of an aforementioned fullerene-derived ketolactam (i.e., $C_{60}$-derived ketolactam compounds of formulas I-VI, compounds of formula I-VI wherein one or more additional addends are bonded to the fullerene cage, and the corresponding $C_{70}$, $C_{76}$, $C_{78}$, $C_{84}$, or $C_{90}$ analogs thereof) as antioxidants.

Another aspect of the present invention relates to the use of an aforementioned fullerene-derived ketolactam (i.e., $C_{60}$-derived ketolactam compounds of formulas I-VI, compounds of formula I-VI wherein one or more additional addends are bonded to the fullerene cage, and the corresponding $C_{70}$, $C_{76}$, $C_{78}$, $C_{84}$, or $C_{90}$ analogs thereof) as internal or topical anti-inflammatory agents in animals or humans.

Another aspect of the present invention relates to the use of an aforementioned fullerene-derived ketolactam (i.e., $C_{60}$-derived ketolactam compounds of formulas I-VI, compounds of formula I-VI wherein one or more additional addends are bonded to the fullerene cage, and the corresponding $C_{70}$, $C_{76}$, $C_{78}$, $C_{84}$, or $C_{90}$ analogs thereof) on the skin of animals or humans.

Another aspect of the present invention relates to the use of an aforementioned fullerene-derived ketolactam (i.e., $C_{60}$-derived ketolactam compounds of formulas I-VI, compounds of formula I-VI wherein one or more additional addends are bonded to the fullerene cage, and the corresponding $C_{70}$, $C_{76}$, $C_{78}$, $C_{84}$, or $C_{90}$ analogs thereof) for the prevention, remediation, and/or to improve the appearance of inflammatory conditions of the skin in animals or humans.

In certain embodiments, the present invention relates to the aforementioned use, wherein the inflammatory condition is psoriasis, eczema, rosacea, sun-burn, allergic response, sepsis, dermatomyositis, radiation induced erythema, chemically induced erythema, or laser induced erythema.

Another aspect of the present invention relates to the use of an aforementioned fullerene-derived ketolactam (i.e., $C_{60}$-derived ketolactam compounds of formulas I-VI, compounds of formula I-VI wherein one or more additional addends are bonded to the fullerene cage, and the corresponding $C_{70}$, $C_{76}$, $C_{78}$, $C_{84}$, or $C_{90}$ analogs thereof) to improve the appearance of acne in humans, for the prevention of acne in humans, for the remediation of acne in humans, or for any combination thereof.

Certain Additional Compositions of the Invention

In certain embodiments, the present invention relates to a $C_x$ fullerene-derived ketolactam represented by formula I:

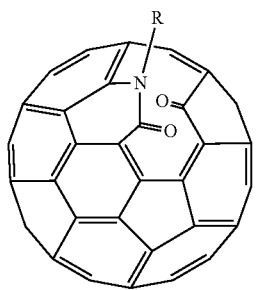

I wherein x is 60, 70, 76, 78, 84, or 90; R is a $C_1$-$C_{50}$ hydrocarbon chain, branched or unbranched, with unsaturation from zero up to maximal, optionally substituted with one aryl group, heteroaryl group, halogen atom, hydroxyl group, a branched or unbranched, with unsaturation from zero up to maximal alkoxy group, or a branched or unbranched, with unsaturation from zero up to maximal alkanoyloxy group, said aryl or heteroaryl being optionally substituted with a halogen atom, a hydroxyl group, a $C_1$-$C_{50}$ hydrocarbon chain, branched or unbranched, with unsaturation from zero up to maximal alkyl group, a $C_1$-$C_{50}$, linear alkoxy group, a $C_9$-$C_{50}$ branched alkoxy group, a $C_1$-$C_{50}$, branched or unbranched, with unsaturation from one up to maximal alkoxy group, a $C_1$-$C_{50}$, branched or unbranched, with unsaturation from zero up to maximal alkanoyloxy group, or a —O(CH$_2$CH$_2$O)$_n$R' group; n is 1 to 100 inclusive; and R' is H, aryl, or a $C_1$-$C_{50}$ hydrocarbon chain, branched or unbranched, with unsaturation from zero up to maximal.

In certain other embodiments, the present invention relates to a $C_x$ fullerene-derived ketolactam represented by formula I:

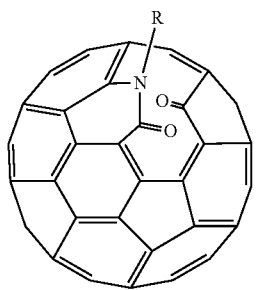

I wherein x is 60, 70, 76, 78, 84, or 90; R is a $C_1$-$C_{50}$ hydrocarbon chain, branched or unbranched, with unsaturation from zero up to maximal, optionally substituted with one aryl group, heteroaryl group, halogen atom, hydroxyl group, a branched or unbranched, with unsaturation from zero up to maximal alkoxy group, or a branched or unbranched, with unsaturation from zero up to maximal alkanoyloxy group, said aryl or heteroaryl being optionally substituted with two or more groups, independently selected from the group consisting of halogen atoms, hydroxyl groups, $C_1$-$C_{50}$ hydrocarbon chains, branched or unbranched, with unsaturation from zero up to maximal alkyl group, $C_1$-$C_{50}$, branched or unbranched, with unsaturation from zero up to maximal alkoxy groups, $C_1$-$C_{50}$, branched or unbranched, with unsaturation from zero up to maximal alkanoyloxy groups, or —O(CH$_2$CH$_2$O)$_n$R' groups; n is 1 to 100 inclusive; and R' is H, aryl, or a $C_1$-$C_{50}$ hydrocarbon chain, branched or unbranched, with unsaturation from zero up to maximal. In certain embodiments, R may be a $C_9$-$C_{50}$ branched alkoxy group.

In still other embodiments, the present invention relates to a $C_x$ fullerene-derived ketolactam represented by formula I:

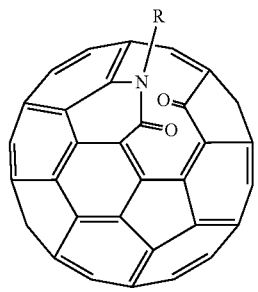

I wherein x is 60, 70, 76, 78, 84, or 90; R is a $C_1$-$C_{50}$ hydrocarbon chain, branched or unbranched, with unsaturation from zero up to maximal, optionally substituted with two or more aryl groups, heteroaryl groups, halogen atoms, hydroxyl groups, branched or unbranched, with unsaturation from zero up to maximal alkoxy groups, or branched or unbranched, with unsaturation from zero up to maximal alkanoyloxy groups, said aryls or heteroaryls being optionally substituted with one or more groups, independently selected from the group consisting of halogen atoms, hydroxyl groups, $C_1$-$C_{50}$ hydrocarbon chains, branched or unbranched, with unsaturation from zero up to maximal alkyl group, $C_1$-$C_{50}$, branched or unbranched, with unsaturation from zero up to maximal alkoxy groups, $C_1$-$C_{50}$, branched or unbranched, with unsaturation from zero up to maximal alkanoyloxy groups, or —O(CH$_2$CH$_2$O)$_n$R' groups; n is 1 to 100 inclusive; and R' is H, aryl, or a $C_1$-$C_{50}$ hydrocarbon chain, branched or unbranched, with unsaturation from zero up to maximal. In certain embodiments, R may be a $C_9$-$C_{50}$ branched alkoxy group.

In yet other embodiments, the present invention relates to a $C_x$ fullerene-derived ketolactam represented by formula I:

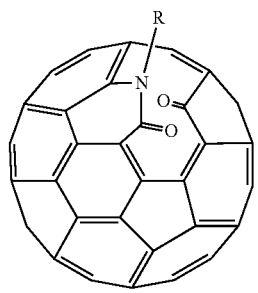

I wherein x is 60, 70, 76, 78, 84, or 90; R is aryl or heteroaryl, said aryl or heteroaryl being optionally substituted with one or more groups independently selected from the group consisting of halogen atoms, hydroxyl groups, $C_1$-$C_{50}$ linear or branched, with unsaturation from zero up to maximal alkyl groups, $C_1$-$C_{50}$ linear or branched, with unsaturation from zero up to maximal alkoxy groups, $C_1$-$C_{50}$ branched or unbranched, with unsaturation from zero up to maximal alkanoyloxy groups, or —$O(CH_2CH_2O)_nR'$ groups; n is 1 to 100 inclusive; and R' is H, aryl, or a $C_1$-$C_{50}$ hydrocarbon chain, branched or unbranched, with unsaturation from zero up to maximal.

In certain embodiments, R may be a $C_9$-$C_{50}$ branched alkoxy group.

In other embodiments, the present invention relates to a $C_x$ fullerene-derived ketolactam represented by formula II:

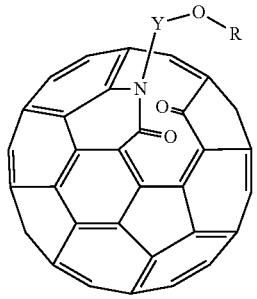

II wherein x is 60, 70, 76, 78, 84, or 90; Y is a $C_1$-$C_{50}$ hydrocarbon chain, branched or unbranched, with unsaturation from zero up to maximal; R is aryl or heteroaryl, said aryl or heteroaryl being optionally substituted with one or more groups independently selected from the group consisting of halogen atoms, hydroxyl groups, $C_1$-$C_{50}$ linear or branched, with unsaturation from zero up to maximal alkyl groups, $C_1$-$C_{50}$ linear or branched, with unsaturation from zero up to maximal alkoxy groups, $C_1$-$C_{50}$ branched or unbranched, with unsaturation from zero up to maximal alkanoyloxy groups, or —$O(CH_2CH_2O)_nR'$ groups; n is 1 to 100 inclusive; and R' is hydrogen, aryl, or a $C_1$-$C_{50}$ hydrocarbon chain, branched or unbranched, with unsaturation from zero up to maximal. In certain embodiments, R may be a $C_9$-$C_{50}$ branched alkoxy group.

In some embodiments, the present invention relates to the compound represented by formula III:

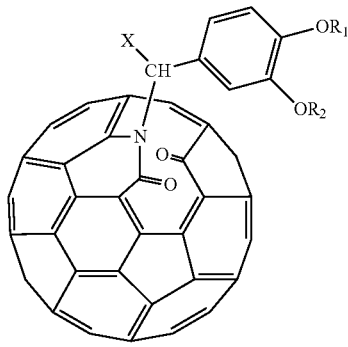

III wherein x is 60, 70, 76, 78, 84, or 90; X is H or a $C_1$-$C_{50}$ linear or branched, with unsaturation from zero up to maximal alkyl group; $R_1$ is H, a $C_1$-$C_{50}$ linear or branched, with unsaturation from zero up to maximal alkyl group, or $O(CH_2CH_2O)_mR''$; m is 1 to 100 inclusive; R'' is H, aryl, or a $C_1$-$C_{50}$ hydrocarbon chain, branched or unbranched, with unsaturation from zero up to maximal; $R_2$ is H, a $C_1$-$C_{50}$ linear or branched, with unsaturation from zero up to maximal alkyl group, or $O(CH_2CH_2O)_pR'''$; p is 1 to 100 inclusive; and R''' is H, aryl, or a $C_1$-$C_{50}$ hydrocarbon chain, branched or unbranched, with unsaturation from zero up to maximal. In some embodiments, X is H or alkyl; $R_1$ is $C_{10}$-$C_{24}$ alkyl; and $R_2$ is $CH_3$. In some embodiments, X is H; $R_1$ is a $C_{22}$ alkyl; and $R_2$ is $CH_3$. In some embodiments, X is H; $R_1$ is a $C_{16}$ alkyl; and $R_2$ is $CH_3$. In certain embodiments, R may be a $C_9$-$C_{50}$ branched alkoxy group.

In other embodiments, the present invention relates to a $C_x$ fullerene-derived ketolactam represented by formula IV:

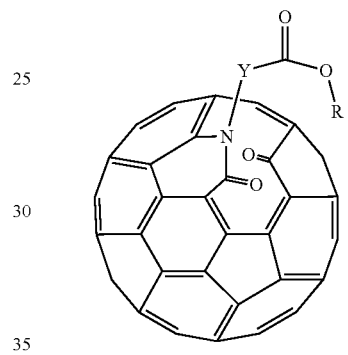

IV wherein x is 60, 70, 76, 78, 84, or 90; Y is a $C_1$-$C_{50}$ hydrocarbon chain, branched or unbranched, with unsaturation from zero up to maximal; R is selected from the group consisting of H, a $C_1$-$C_{50}$ hydrocarbon chain, branched or unbranched, with unsaturation from zero up to maximal, aryl, and heteroaryl, said hydrocarbon chain, aryl, or heteroaryl, being optionally substituted with one or more groups independently selected from the group consisting of halogen atoms, hydroxyl groups, $C_1$-$C_{50}$ linear or branched, with unsaturation from zero up to maximal alkyl groups, $C_1$-$C_{50}$ linear or branched, with unsaturation from zero up to maximal alkoxy groups, $C_1$-$C_{50}$ branched or unbranched, with unsaturation from zero up to maximal alkanoyloxy groups, or —$O(CH_2CH_2O)_nR'$ groups; n is 1 to 100 inclusive; and R' is hydrogen, aryl, or a $C_1$-$C_{50}$ hydrocarbon chain, branched or unbranched, with unsaturation from zero up to maximal. In certain embodiments, R may be a $C_9$-$C_{50}$ branched alkoxy group.

In certain other embodiments, the present invention relates to a $C_x$ fullerene-derived ketolactam represented by formula V:

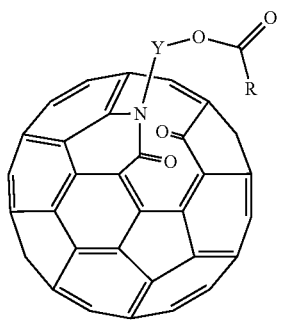

wherein x is 60, 70, 76, 78, 84, or 90; Y is a $C_1$-$C_{50}$ hydrocarbon chain, branched or unbranched, with unsaturation from zero up to maximal; R is selected from the group consisting of H, a $C_1$-$C_{50}$ hydrocarbon chain, branched or unbranched, with unsaturation from zero up to maximal, aryl, and heteroaryl, said hydrocarbon chain, aryl, or heteroaryl, being optionally substituted with one or more groups independently selected from the group consisting of halogen atoms, hydroxyl groups, $C_1$-$C_{50}$ linear or branched, with unsaturation from zero up to maximal alkyl groups, $C_1$-$C_{50}$ linear or branched, with unsaturation from zero up to maximal alkoxy groups, $C_1$-$C_{50}$ branched or unbranched, with unsaturation from zero up to maximal alkanoyloxy groups, or —O(CH$_2$CH$_2$O)$_n$R' groups; n is 1 to 100 inclusive; and R' is hydrogen, aryl, or a $C_1$-$C_{50}$ hydrocarbon chain, branched or unbranched, with unsaturation from zero up to maximal. In certain embodiments, R may be a $C_9$-$C_{50}$ branched alkoxy group.

In yet other embodiments, the present invention relates to a $C_x$ fullerene-derived ketolactam represented by formula VI:

VI

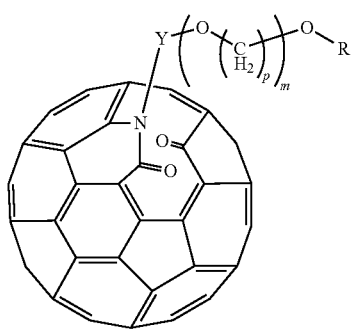

wherein x is 60, 70, 76, 78, 84, or 90; Y is a $C_1$-$C_{50}$ hydrocarbon chain, branched or unbranched, with unsaturation from zero up to maximal; m is 1 to 100 inclusive; p is 2 or 3; R is independently selected from the group consisting of H, a $C_1$-$C_{50}$ hydrocarbon chain, branched or unbranched, with unsaturation from zero up to maximal, aryl, and heteroaryl, said hydrocarbon chain, aryl, or heteroaryl, being optionally substituted with one or more groups independently selected from the group consisting of halogen atoms, hydroxyl groups, $C_1$-$C_{50}$ linear or branched, with unsaturation from zero up to maximal alkyl groups, $C_1$-$C_{50}$ linear or branched, with unsaturation from zero up to maximal alkoxy groups, $C_1$-$C_{50}$ branched or unbranched, with unsaturation from zero up to maximal alkanoyloxy groups, or —O(CH$_2$CH$_2$O)$_n$R' groups; n is 1 to 100 inclusive; and R' is hydrogen, aryl, or a $C_1$-$C_{50}$ hydrocarbon chain, branched or unbranched, with unsaturation from zero up to maximal. In certain embodiments, R may be a $C_9$-$C_{50}$ branched alkoxy group.

In other embodiments, the present invention relates to a $C_x$ fullerene-derived ketolactam represented by formula VI:

VI

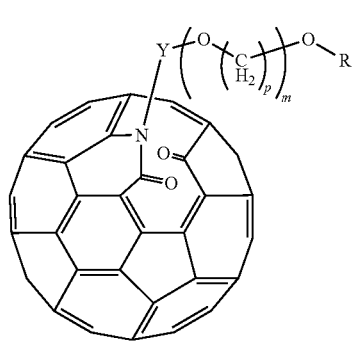

wherein x is 60, 70, 76, 78, 84, or 90; Y is a $C_1$-$C_{50}$ hydrocarbon chain, branched or unbranched, with unsaturation from zero up to maximal; m is 1 to 100 inclusive; p is 2 or 3; R is —C(O)—X; X is selected from the group consisting of H, a $C_1$-$C_{50}$ hydrocarbon chain, branched or unbranched, with unsaturation from zero up to maximal, aryl, and heteroaryl, said hydrocarbon chain, aryl, or heteroaryl, being optionally substituted with one or more groups independently selected from the group consisting of halogen atoms, hydroxyl groups, $C_1$-$C_{50}$ linear or branched, with unsaturation from zero up to maximal alkyl groups, $C_1$-$C_{50}$ linear or branched, with unsaturation from zero up to maximal alkoxy groups, $C_1$-$C_{50}$ branched or unbranched, with unsaturation from zero up to maximal alkanoyloxy groups, or —O(CH$_2$CH$_2$O)$_n$R' groups; n is 1 to 100 inclusive; and R' is hydrogen, aryl, or a $C_1$-$C_{50}$ hydrocarbon chain, branched or unbranched, with unsaturation from zero up to maximal. In certain embodiments, R may be a $C_9$-$C_{50}$ branched alkoxy group.

EXEMPLIFICATION

The present description is further illustrated by the following examples, which should not be construed as limiting in any way.

Example 1—Synthesis of Fullerene-Derived Ketolactam Derivative HG2-V1

Figure 9:
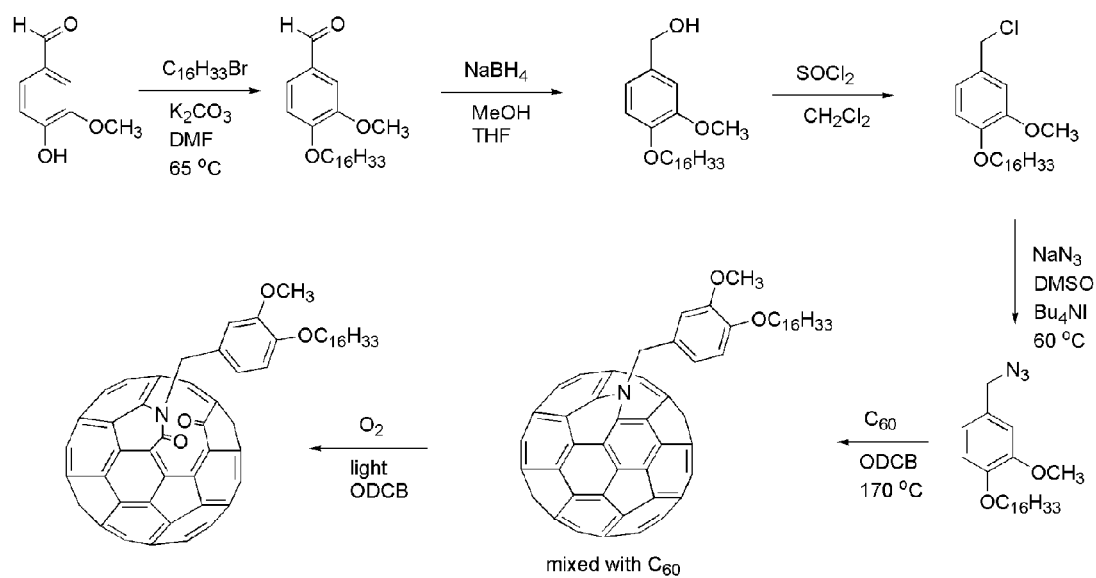
FIG. 9 depicts a synthesis of fullerene-derived ketolactam derivative HG2-V1.
Figure 10:
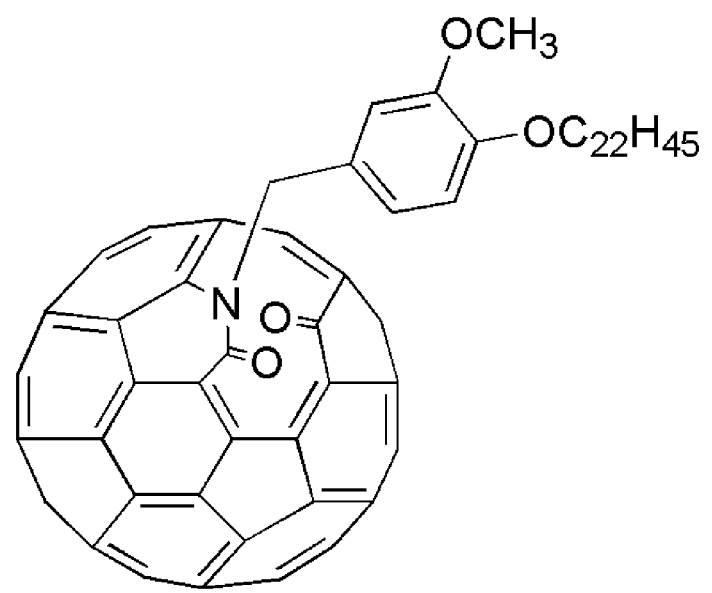
FIG. 10 depicts fullerene-derived ketolactam HG2-V2.

The fullerene-derived ketolactam derivative HG2-V1 was synthesized by the route as depicted in FIG. 9. The synthesis is based on procedures that have been published in literature for comparable compounds (see, for example, a) P. Chritchley and G. J. Clarkson, *Organic and Biomolecular Chemistry* 2003, 1, 4148; and b) C. J. Brabec et al., *Advanced Functional Materials* 2001, 11, 374).

[a] Synthesis of 4-hexadecyloxy-3-methoxy-benzaldehyde. A mixture of 3.05 g of vanilline, 6.11 g of hexadecylbromide, 30 mg of tetrabutylammonium iodide and 3.10 g of potassium carbonate in 35 mL of DMF was heated at 65° C. under an N$_2$ atmosphere for 66 h. The reaction mixture was cooled down to room temperature and mixed with 120 mL of water. The aqueous layer was extracted with ether (1×150 mL, subsequently 3×50 mL). The organic layers were combined and washed subsequently with a saturated NaHCO$_3$ solution (25 mL), water (25 mL), and brine (25 mL). Drying over Na$_2$SO$_4$ and removal of the solvent in vacuo gave 7.32 g of crude product. This was recrystallized from 50 mL of methanol to give 6.93 g of 4-hexadecyloxy-3-methoxy-benzaldehyde as a white powder. $^1$H NMR (300 MHz, CDCl$_3$): δ 9.85 (s, 1H); 7.45-7.40 (m, 2H); 6.96 (d, 1H, J=8.0 Hz); 4.10 (t, 2H, J=6.8 Hz); 3.93 (s, 3H); 1.92-1.82 (m, 2H); 1.52-1.20 (m, 26H); 0.88 (t, 3H, J=7.0 Hz) ppm. $^{13}$C NMR (75 MHz, CDCl$_3$): δ 190.90; 154.21; 149.86; 129.86; 126.80; 111.36; 109.26; 69.20; 56.03; 31.91; 29.68 (large signal); 29.58; 29.52; 29.34; 28.90; 25.88; 22.69; 14.11 ppm. IR (KBr, cm$^{-1}$): 3003 (m); 2913 (s); 2849 (s); 1676 (s); 1597 (m); 1585 (s); 1512 (s) 1273 (m); 1239 (m).

[b] Synthesis of 4-hexadecyloxy-3-methoxy-benzyl alcohol. To a solution of 3.01 g 4-hexadecyloxy-3-methoxy-benzaldehyde in a mixture of 25 mL of methanol and 50 mL of tetrahydrofuran was added 310 mg of NaBH$_4$. The reaction was stirred overnight and quenched it into 350 mL of ice water. The product was isolated by filtration and recrystallized from methanol. This gave 2.63 g of 4-hexadecyloxy-3-methoxy-benzyl alcohol as a fine white powder. $^1$H NMR (300 MHz, CDCl$_3$): δ 6.93 (s, 1H); 6.90-6.83 (m, 2H); 4.62 (s, 2H); 4.00 (t, 2H, J=6.9 Hz); 3.88 (s, 3H); 1.89-1.78 (m, 2H); 1.50-1.22 (m, 26H); 0.88 (t, 3H, J=6.9 Hz) ppm. $^{13}$C NMR (75 MHz, CDCl$_3$): δ 149.43; 148.06; 133.46; 119.35; 112.70; 110.82; 69.07; 65.24; 55.87; 31.87; 29.63 (large signal); 29.55; 29.52; 29.36; 29.31; 29.10; 25.90; 22.64; 14.07 ppm. IR (KBr, cm$^{-1}$): 3350 (m, br.); 3008 (w); 2953 (m); 2917 (m); 2848 (m); 1612 (w); 1590 (m); 1518 (m); 1467 (m); 1254 (m); 1237 (m).

[c] Synthesis of 4-hexadecyloxy-3-methoxy-benzyl chloride. To a solution of 2.55 g of 4-hexadecyloxy-3-methoxy-benzyl alcohol in 40 mL of dichloromethane was added 1.0 mL of thionyl chloride. The resulting mixture was stirred for 22 h. The reaction was quenched by pouring the solution into 25 mL of water. The layers were separated and the aqueous layer was extracted with ether (3×25 mL). The organic layers were combined, washed twice with brine, and dried over Na$_2$SO$_4$. Removal of the solvents in vacuo gave 3.3 g of a dark oil that solidified upon standing, giving a brown solid. Recrystallization from acetonitrile gave 1.85 g of 4-hexadecyloxy-3-methoxy-benzyl chloride as a light brown powder. $^1$H NMR (300 MHz, CDCl$_3$): δ 6.93-6.80 (br. m, 3H); 4.57 (s, 2H); 4.01 (t, 2H, J=6.8 Hz); 1.87-1.79 (m, 2H); 1.49-1.21 (m, 26H); 0.88 (t, 3H, J=6.9 Hz) ppm. $^{13}$C NMR (50 MHz, CDCl$_3$): δ 149.50; 148.83; 129.83; 121.12; 112.59; 112.18; 69.07; 55.99; 46.70; 31.90; 29.66 (large signal); 29.57; 29.35; 29.09; 25.92; 22.66; 14.08 ppm. IR (KBr, cm$^{-1}$): 2997 (w); 2917 (m); 2849 (m); 1605 (w); 1591 (w); 1519 (m); 1465 (m); 1270 (m); 1240 (m).

[d] Synthesis of 4-hexadecyloxy-3-methoxy-benzyl azide. A mixture of 1.78 g of 4-hexadecyloxy-3-methoxy-benzyl chloride, 293 mg of NaN$_3$ and a catalytic amount of Bu$_4$NI in 20 mL of DMSO was heated at 60° C. for 42 h. The reaction mixture was cooled down to room temperature and mixed with 75 mL of ice water. The crude product was isolated by filtration and redissolved in ether (50 mL). This solution was washed with a small amount of brine and dried over Na$_2$SO$_4$. Removal of the solvent in vacuo gave 1.72 g of a dark oil that solidified upon standing, giving a brown solid. Column chromatography (silica gel, petroleum ether/ether 95/5 (v/v)) was used to isolate the product. All solutions containing the desired benzyl azide were combined and the resulting solution was decolorized using activated carbon. Drying over Na$_2$SO$_4$ and removal of the solvents in vacuo gave 1.70 g of 4-hexadecyloxy-3-methoxy-benzyl azide as an off-white solid. $^1$H NMR (300 MHz, CDCl$_3$): δ 6.90-6.82 (m, 3H); 4.27 (s, 2H); 4.01 (t, 2H, J=6.7 Hz); 3.88 (s, 3H); 1.89-1.79 (m, 2H); 1.52-1.21 (m, 26H); 0.88 (t, 3H, J=6.6 Hz) ppm. $^{13}$C NMR (75 MHz, CDCl$_3$): δ 149.57; 148.68; 127.63; 120.80; 112.64; 111.75; 69.04; 55.99; 54.81; 31.92; 29.69 (large signal); 29.60; 29.40; 29.35; 29.13; 25.94; 22.69; 14.13 ppm. IR (KBr, cm$^{-1}$): 2998 (w); 2916 (m); 2849 (m); 2099 (m); 1589 (w); 1517 (m); 1468 (m); 1267 (m); 1238 (m).

[e] Synthesis of HG2-V1. A solution of C$_{60}$ (2.17 g) in o-dichlorobenzene (450 mL) under N$_2$ was heated to 150° C. Subsequently, 4-hexadecyloxy-3-methoxy-benzyl azide (1.23 g) was added at once and the resulting mixture was heated to 170° C., and kept at this temperature for approximately 2.5 h. It was cooled down to room temperature and concentrated in vacuo.

The reaction mixture was redissolved in 200 mL of a 1:1 mixture (v/v) of p-xylene and petroleum ether (Bp 80-110° C.) and put on a silica gel column (prepared with p. e. 80-110). The desired azafulleroid was isolated by chromatography using p-xylene/p.e. 80-110 (1:2 (v/v)). This gave a mixture of the crude azafulleroid and C$_{60}$ in a 57/43 ratio, which was directly used in the next step of the synthesis.

The crude azafulleroid was redissolved in o-dichlorobenzene (400 mL). This solution was placed in a large 3-necked flask fitted with a gas inlet, a condenser, and a thermometer. Oxygen was bubbled through the solution, and the reaction mixture was illuminated with a 400 W sodium lamp, with stirring. The conversion of the azafulleroid to the fullerene-derived ketolactam derivative was monitored by HPLC. The conversion was complete after irradiating for 23 h, during which time the temperature rose to 46° C. The reaction mixture was concentrated in vacuo, and the product was purified by column chromatography (silica gel, toluene. The product was suspended in pentane and isolated by centrifugation. Subsequently, it was washed 2× with pentane. Drying in vacuo gave 0.69 g product as a black solid. Of this material, 530 mg was chromatographed and purified a second time, as described above. This gave 435 mg pure HG2-V1 as black, crystalline material. $^1$H NMR (300 MHz, CDCl$_3$): δ 7.11 (d, 1H, J=1.5 Hz); 7.08-7.03 (m, 1H); 6.82 (d, 1H, J=8.1 Hz); 6.34 (d, 1H, J=15.0 Hz); 5.36 (d, 1H, J=14.7 Hz); 3.98 (t, 2H, J=6.9 Hz); 3.86 (s, 3H); 1.84-1.78 (m, 2H); 1.50-1.22 (m, 26H); 0.88 (t, 3H, J=7.1 Hz) ppm. IR (KBr, cm$^{-1}$): 2922 (s); 2850 (s); 2337 (w); 1728 (s); 1688 (s); 1515 (m); 1463 (m); 1261 (m); 1036 (m); 769 (m); 522 (m).

Example 2—Synthesis of Fullerene-Derived Ketolactam HG2-V2

HG2-V2 (CAS#943912-75-2; CA Index Name: 2a-Aza-1,2(2a)-homo-1,9-seco[5,6]fullerene-C$_{60}$—I$_h$-1,9-dione,2a-[[4-docosyloxy)-3-methoxyphenyl]methyl] was prepared in a method directly analogous to HG2-V1, the only difference being the substitution of C$_{22}$H$_{45}$Br in place of C$_{16}$H$_{33}$Br. Comparable yields were obtained. $^1$H NMR (300 MHz, CDCl$_3$): δ 7.11 (d, 1H, J=1.8 Hz); 7.08-7.03 (m, 1H); 6.82 (d, 1H, J=8.4 Hz); 6.34 (d, 1H, J=14.6 Hz); 5.36 (d, 1H, J=15.0 Hz); 3.97 (t, 2H, J=6.8 Hz); 3.86 (s, 3H); 1.84-1.78 (m, 2H); 1.50-1.22 (m, 38H); 0.88 (t, 3H, J=6.6 Hz) ppm. IR (KBr, cm$^{-1}$): 2922 (s); 2851 (s); 2336 (w); 1728 (s); 1688 (s); 1515 (m); 1463 (m); 1261 (m); 1037 (m); 769 (m); 522 (m).

Examples 1 and 2 describe the synthesis of two fullerene-derived ketolactam molecules. As described throughout the specification, other fullerene-derived ketolactam molecules are contemplated. Also contemplated are fullerene-derived ketolactam derivative molecules, where one or more addends are chemically bonded to the fullerene cage of the fullerene-derived ketolactam. Non-limiting examples of such fullerene-derived ketolactam derivatives are fullerene-derived ketolactam methano derivatives, fullerene-derived ketolactam pyrrolidine derivatives, and fullerene-derived ketolactam epoxide derivatives.

In some embodiments, the addend may be chemically bonded to a fullerene derived ketolactam. In other embodiments, the addend may be chemically bonded to a fullerene, which may then be used as a reactant for the production of a fullerene-derived ketolactam derivative.

Figure 11:
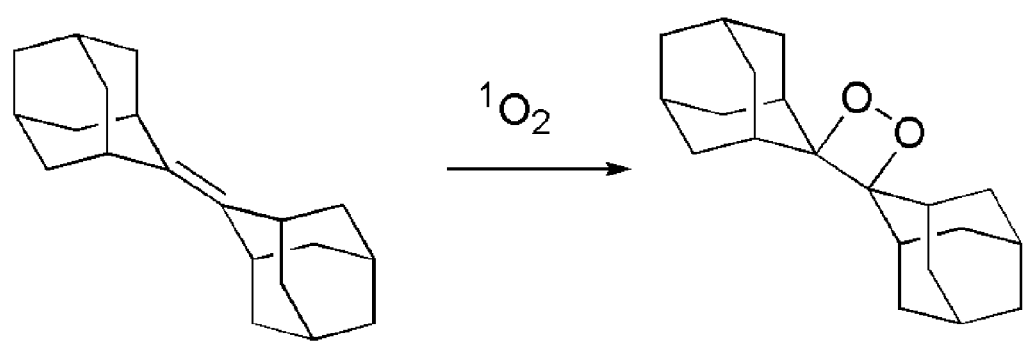
FIG. 11 depicts the reaction of admantylideneadamantane (ad=ad) with $^1O_2$ to give a stable 1,2-dioxetane, adamantylideneadamantane peroxide. See Wieringa, J. H. et al., Tetrahedron Letters, 2, 169, 1972.

Example 3—Comparison of the $^1O_2$ and Superoxide Generation Rate of Fullerene Derivatives and Fullerene-Derived Ketolactams: Photo-Oxidation of Adamantylideneadamantane Fullerenes are known to produce $^1O_2$ upon illumination by the reaction sequence:
Fullerene+light→excited fullerene, singlet
Excited fullerene, singlet→excited fullerene, triplet
Excited fullerene, triplet+$O_2$→fullerene+singlet oxygen ($^1O_2$) The $^1O_2$ thus generated can react with a fullerene, giving an oxidized fullerene, or with other molecules that can react with $^1O_2$. One such molecule is adamantylideneadamantane (ad=ad), which is known to react with $^1O_2$, giving a stable 1,2-dioxetane, adamantylideneadamantane peroxide, as the product (J. H. Wieringa et al., *Tetrahedron Letters* 1972, 2, 169). This reaction is depicted in FIG. 11. This oxidation of ad=ad can be used to monitor the formation of $^1O_2$ by fullerenes or fullerene derivatives.

In a first set of experiments, Phenyl-$C_{61}$-Butyric-Acid-Methyl-Ester (PCBM,) and HG2-V1 were compared. A dilute solution of ad=ad in chlorobenzene (1.5 mg/mL) containing a small amount of the fullerene derivative was irradiated with a Na lamp, while bubbling air through the solution. Details are described in Experiments 1 and 2 below. After reaction overnight, the solvent was removed in vacuo and the residual material analyzed by $^1H$ NMR. This showed the formation of the dioxetane compound, as evidenced from the appearance of a signal at 2.65 ppm. The amount of adamantylideneadamantane peroxide formed when PCBM was used was much larger than that formed when using HG2-V1. Since the molar amounts of fullerene derivative used are comparable, this result indicates that HG2-V1 generates less $^1O_2$ than PCBM. In both cases, most of the fullerene material had been photobleached after the illumination.

In a second set of experiments, the above reaction was done at a high concentration (20 mg/mL) of ad=ad, this time using $CCl_4$ as the solvent. The advantage of $CCl_4$ is that this solvent does not show any signals in $^1H$ NMR spectra. The high concentration of ad=ad allows for easy measurements and makes it possible to see small percentages of dioxetane that are formed. Thus, samples from the reaction can be directly analyzed by $^1H$ NMR, when diluted with, e.g., $CDCl_3$. This allows for monitoring the formation of the dioxetane compound over time.

The results from these experiments (Experiments 3 and 4 below) show that the production of adamantylideneadamantane peroxide proceeds much faster with PCBM compared to HG2-V1, and also that more of the dioxetane compound is produced when using PCBM. The results are depicted in the graph below. The graph displays the ratio of the peak at 2.65 ppm and the signal at 2.88 ppm of ad=ad. As before, the fullerenes were oxidized to a large extent after the reaction, which is why the formation of the dioxetane almost stops at long irradiation times. These results again indicate that HG2-V1 produces less $^1O_2$ than PCBM.

[a] Experiment 1. A solution of adamantylideneadamantane (150 mg) and PCBM (4.9 mg) in chlorobenzene (100 mL) was placed in a 3-necked flask fitted with a thermometer, a gas inlet, a magnetic stir bar, and a condenser. Then, the solution was illuminated (with stirring) for 17 h using a 400 W sodium lamp at close range, while bubbling air through the solution. During this time, the temperature of the solution rose to 37° C.

The lamp was switched off and the reaction mixture was cooled down and concentrated in vacuo to give an off-white solid. Subsequently, some of this solid material was scraped out using a spatula, dissolved in $CDCl_3$ and investigated by $^1H$ NMR. This showed the formation of a substantial amount of adamantylideneadamantane peroxide, as evidenced by the broad signal at 2.65 ppm.

[b] Experiment 2. A solution of adamantylideneadamantane (152 mg) and HG2-V1 (5.8 mg) in chlorobenzene (100 mL) was placed in a 3-necked flask fitted with a thermometer, a gas inlet, a magnetic stir bar, and a condenser. Then, the solution was illuminated (with stirring) for 16.5 h using a 400 W sodium lamp at close range, while bubbling air through the solution. During this reaction, the temperature of the solution rose to 45° C.

The lamp was switched off and the reaction mixture was cooled down and concentrated in vacuo to give an off-white solid. Subsequently, some of this solid material was scraped out using a spatula, dissolved in $CDCl_3$ and investigated by $^1H$ NMR. This showed the formation of adamantylideneadamantane peroxide, as evidenced by the broad signal at 2.65 ppm. The relative amount of peroxide formed was, however, considerably smaller than that obtained when using PCBM as the dye generating $^1O_2$ (see Experiment 1 above).

[c] Experiment 3. A solution of adamantylideneadamantane (403 mg) and PCBM (2.1 mg) in tetrachloromethane (20 mL) was placed in a 3-necked flask fitted with a thermometer, a gas inlet, a magnetic stir bar, and a condenser. Then, the solution was illuminated (with stirring) using a 150 W sodium lamp at close range (~6 cm distance), while bubbling air through the solution. During this reaction, the temperature of the solution rose to 36° C.

Samples of 150-200 µL were taken from the reaction and diluted with ~400 µL of $CDCl_3$. Subsequently these solutions were investigated by $^1H$ NMR. Thus, the formation of adamantylideneadamantane peroxide was monitored over time, by following the appearance of the signal at 2.65 ppm.

[d] Experiment 4. A solution of adamantylideneadamantane (402 mg) and HG2-V1 (2.7 mg) in tetrachloromethane (20 mL) was placed in a 3-necked flask fitted with a thermometer, a gas inlet, a magnetic stir bar, and a condenser. Then, the solution was illuminated (with stirring) using a 150 W sodium lamp at close range (~6 cm distance), while bubbling air through the solution. During this reaction, the temperature of the solution rose to 37° C. The (setup of the) equipment used for this reaction was the same as used in Experiment 3.

Samples of 150-200 µL were taken from the reaction and diluted with ~400 µL of $CDCl_3$. Subsequently these solutions were investigated by $^1H$ NMR. Thus, the formation of adamantylideneadamantane peroxide was monitored over time, by following the appearance of the signal at 2.65 ppm.

Figure 12:
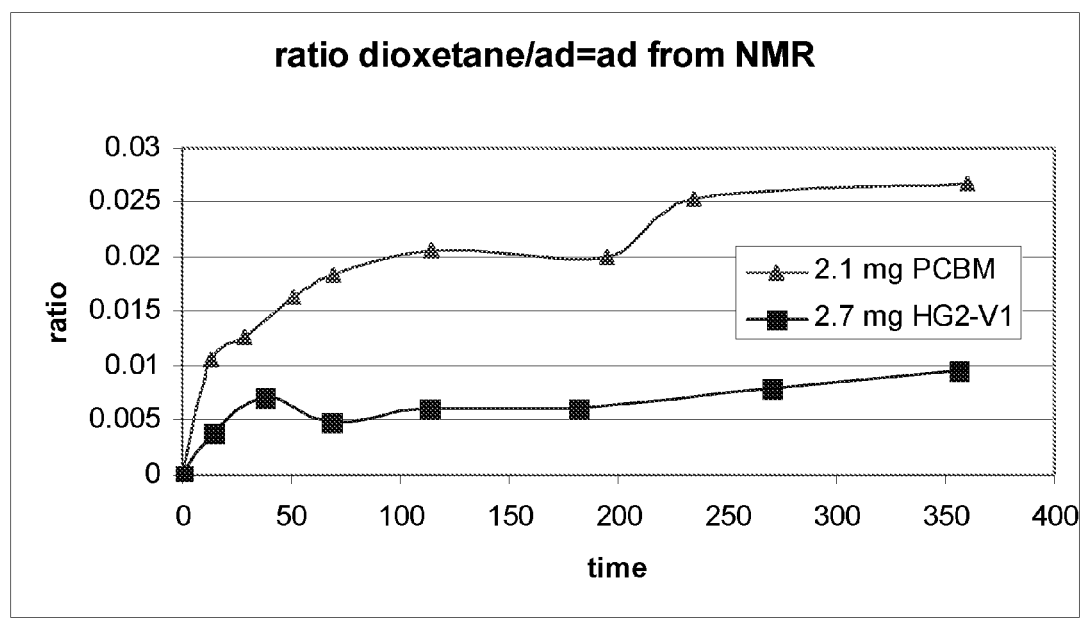
FIG. 12 depicts a graph comparing singlet oxygen generation capacity of PCBM and HGV2-V2.

At the initial data point of 13 minutes (PCBM) and 14 minutes (HG2-V1), it was observed that both solutions were still clear, with no visible solids or color change, indicating that little photobleaching of either compound had occurred. The concentrations of each can be assumed to be constant and equal to the starting concentrations, which were of equal molarity. Since ad=ad is in large excess, its concentration can also be assumed to be constant. FIG. 12 shows the ratio of the dioxetane product to the ad=ad reactant. It can be seen that much less oxidation product of the ad=ad+singlet oxygen reaction is formed by the HG2-V1 compared to PCBM. As the ad=ad and PCBM or HG2-V1 concentrations can all be assumed to be constant, the ratio of the slopes of the initial rate of formation of the dioxetane product can be used to give a semi-quantitative measure of the overall $^1O_2$ generation capacity. Since the extinction coefficients of PCBM and HG2-V1 are approximately equal for the visible wavelengths used (from the Na lamp), then the ratio of the slopes is approximately equal to the ratio of the net generation of $^1O_2$. Taking this ratio gives the result that the net generation of $^1O_2$ of HG2-V1 is about 0.2-0.3 of the net generation of $^1O_2$ of PCBM.

[e] Two beakers were irradiated simultaneously with a UV light source (Philips HB172, fitted with 4 Philips Cleo 15 W luminescent tubes; UV-type 3). Beaker 1 contained a mixture of 301.0 mg of adamantylideneadamantane and 24.9 mg of α-tocopherol (Aldrich, >97%) in 100 mL of chlorobenzene. This solution was placed in a 250 mL beaker, which was wrapped with paper and Al-foil to prevent light going through the side of the beaker. The solution was stirred magnetically and irradiated 7 hours with a UV lamp (Philips HB172, fitted with 4 Philips Cleo 15 W luminescent tubes; UV-type 3), which was mounted horizontally directly above the beakers. The reaction mixture was concentrated in vacuo and the resulting solid material was analyzed by $^1H$ NMR spectroscopy as described above. This showed the formation of adamantylideneadamantane peroxide, as evidenced by the broad signal at 2.65 ppm. The ratio of the integrals of unreacted adamantylideneadamantane (at 2.9 ppm) to adamantylideneadamantane peroxide was 90:10.

Beaker 2 contained a mixture of 301.2 mg of adamantylideneadamantane and 25.0 mg of HG2-V2 in 100 mL of chlorobenzene. This solution was placed in a 250 mL beaker, which was wrapped with paper and Al-foil to prevent light going through the side of the beaker. The solution was stirred magnetically and irradiated 7 hours with a UV lamp (Philips HB172 fitted with 4 Philips Cleo 15 W luminescent tubes; UV-type 3), which was mounted horizontally directly above the beakers. The reaction mixture was concentrated in vacuo and the resulting solid material was analyzed by $^1H$ NMR spectroscopy as described above. This showed the formation of adamantylideneadamantane peroxide, as evidenced by the broad signal at 2.65 ppm. The ratio of the integrals of unreacted adamantylideneadamantane (at 2.9 ppm) to adamantylideneadamantane peroxide was 94:6.

This example demonstrates that the net generation of $^1O_2$ under UV irradiation, of equal weight percentage formulations, is less for HG2-V2 than α-tocopherol.

[f] Two beakers were irradiated simultaneously by natural sunlight. Beaker 2 contained a solution of 300.5 mg of adad and 17.9 mg of PCBM in 100 mL of chlorobenzene. This solution was placed in a 250 mL beaker, wrapped with paper and Al-foil to prevent light going through the side of the beaker. The solution was stirred magnetically and placed outside, in Groningen, The Netherlands, on a sunny day in July, from 13.40 pm to 16.30 pm. The resulting solution was put in a brown-glass bottle for transport. The solvent was removed in vacuo and the resulting solid material was analyzed by $^1H$ NMR spectroscopy as described above. This showed the formation of adamantylideneadamantane peroxide, as evidenced by the broad signal at 2.65 ppm. The ratio of the integrals of unreacted adamantylideneadamantane (at 2.9 ppm) to adamantylideneadamantane peroxide was 78:22.

Beaker 2 contained a mixture of 300.7 mg of adad and 8.1 mg of methylene blue (MB) in 100 mL of chlorobenzene. This solution was placed in a 250 mL beaker, wrapped with paper and Al-foil to prevent light going through the side of the beaker. The saturated solution was stirred magnetically and placed outside, in Groningen, The Netherlands, on a sunny day in July, from 13.40 pm to 16.30 pm. The resulting solution was placed in a brown-glass bottle for transport. Approximately 10 mL of the reaction mixture was filtered and put aside. The remaining amount was concentrated in vacuo and the resulting solid material was analyzed by $^1H$ NMR spectroscopy as described above. This showed the formation of adamantylideneadamantane peroxide, as evidenced by the broad signal at 2.65 ppm. The ratio of the integrals of unreacted adamantylideneadamantane (at 2.9 ppm) to adamantylideneadamantane peroxide was 56:44.

The end-concentration of MB in the chlorobenzene was determined by UV-Vis spectroscopy, using the above mentioned filtered solution. This solution gave an absorbance of A=0.14 at 646 nm (against neat chlorobenzene). The extinction coefficient at 646 nm of MB in pyridine is $8 \times 10^4$ (R. B. McKay, Nature 1966, 210, 296-297), meaning that the concentration was approximately $1.8 \times 10^{-3}$ mmol/L, corresponding to 0.67 mg/L (compared to 240 mg/L for HG2-V2 above).

This experiment shows that though the $^1O_2$ quantum yield of MB is ~0.5, about half of PCBM (~1.0), the net generation of $^1O_2$ is 250 times higher for MB than for PCBM on an equimolar basis. The average optical absorption between 400 nm and 700 nm is about 10 times higher for MB compared to PCBM, therefore, MB produces 25 times the amount of $^1O_2$ as PCBM on an equal absorption and equimolar basis, though it has a $^1O_2$ quantum yield half that of PCBM. This demonstrates the effect that the net $^1O_2$ generation of fullerenes is in fact much lower than expected, due to the quenching effects of epoxide reaction products formed by the photooxidation. Therefore, addition of mono- and multi-epoxidized fullerenes, fullerene derivatives, or fullerene-derived ketolactams to a formulation can act to minimize the reaction products of the photoexcited states of the fullerene, fullerene derivative, or fullerene-derived ketolactam.

[g] Generation of superoxide by HG2-V2 was determined. The superoxide tests were based on the trapping of the superoxide radical, $O_2^-$·, by NBT, nitroblue tetrazolium dichloride. The superoxide formed reacts with the NBT, which is light yellow in aqueous solutions, to form (di) formazan, an intensely blue dye. The absorbance around 550 nm of the formazan can be measured by UV-Vis spectroscopy, which is a measure for the amount of superoxide formed. For more information see: C. Auclair and E. Voisin, in CRC Handbook of methods for oxygen radical research, R. A. Greenwald, Eds., CRC Press, Boca Raton, Fla., 1985, p 123-132.

This system has been used to show the formation of the superoxide radical by $C_{60}$—PVP complexes upon irradiation, in a model of a biological environment (Y. Yamakoshi et al., J. Am. Chem. Soc. 2003, 125, 12803). In the NBT superoxide test, a blank reaction takes place due to the NADH initiator used, depending on the exact conditions and reactants used. In the system used by Yamakoshi et al. the blank reaction is present. Therefore, what is actually determined is the additional formation of superoxide by the compound under investigation.

The $C_{60}$/PVP experiments as reported in literature were done on a small scale, using a total volume of only 164 μL. The reaction was scaled to 5 mL, so that it can be performed in reagent tubes, with magnetic stirring. In all reactions, 600 μL of a 1 mM EDTA solution, 0.60 mL of a 2.4 mM NBT solution, and 240 uL of phosphate buffer (pH 7.2, Sigma-Aldrich) were placed in the tube. Subsequently, the following amounts were added: NADH solution: 100 μL; $H_2O$: 3.5 mL. The NADH solution was 1 mg/mL, and prepared by adding 5.0 mL $H_2O$ to a vial containing 5 mg of NADH (~98%, Sigma). Two experiments were performed with this above preparation. In the first, which contained no HG2-V2, the mixture was stirred magnetically (approximately 900 rpm) and illuminated for 1 h. Subsequently, it was diluted with 15 mL of diluted phosphate buffer (4:1 (v/v) of water/commercial phosphate buffer (vide supra)), closed, and stored in the dark until measured.

In the second experiment, 100 Cl of 0.3% (wt.) HG2-V2 in grape seed oil (corresponding to 40 μmolar) was added and sonicated for one hour, resulting in a slightly opaque solution indicating formation of a fine colloidal oil-in-water solution. This solution was then illuminated for 1 h with stirring, as above. After the experiment, the solution was diluted, as above, centrifuged and separated twice to separate the oil phase from the aqueous phase. UV-Vis measurements were done against water.

In both experiments, cooling was provided by immersing the tube in a large ethanol cooling bath (in a 1 L glass beaker) kept at 17±1° C. using a flexible metal cooling rod (Julabo FT901 cooling system) and magnetic stirring. For irradiation, a 60 W white-light spotlight, mounted horizontally on a base plate, was used. The surface of the lamp was placed at a distance of 6 cm from the tube. The lamp was placed in such a way that it was at the same level as the solution in the reagent tube.

Figure 13:
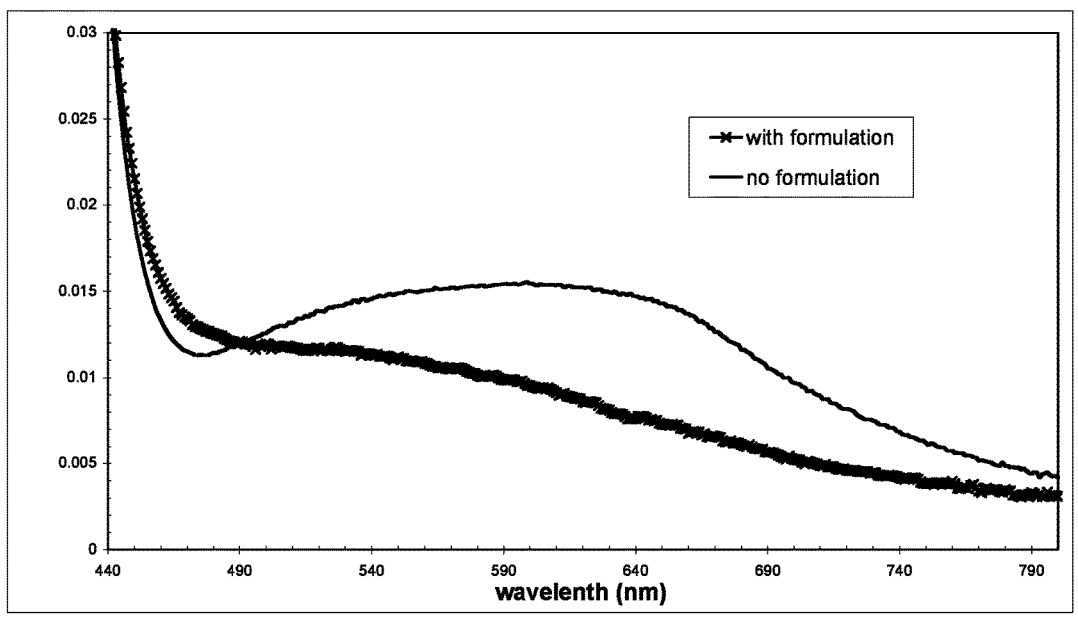
FIG. 13 depicts the UV/Vis spectrum from an experiment to measure the generation of superoxide by HG2-V2.

FIG. 13 shows the UV/Vis spectra for the solution with and without the formulation. Results indicate no additional formation of superoxide compared to the blank, and a significant reduction in superoxide formation, which may or may not be a result of superoxide quenching by the formulation, as the slightly increased opacity caused by the colloidal oil-in-water solution may have decreased the light absorbed by the solution. 40 μmolar C60-PVP by contrast gave a significant increase in the measured optical absorption caused by the dye reaction with superoxide in Yamakoshi et al.

Example 4—Embodiment of an Active of the Present Invention in an Acceptable Carrier 400 mg HG2-V2 was added to 100 g of commercially available liquid grape seed oil and stirred with mechanical stirring for 4 hours at 25 deg. C. The HG2-V2 dissolved to give a clear, dark, amber colored solution of 0.4% (wt.) active in a simple solution. The optical density measured for this solution was over 2 AU/cm, and after 10/1 dilution with toluene was over 0.2. The formulation had a faint grassy scent caused by the grape seed oil Example 5—Embodiment of an Active of the Present Invention in an Acceptable Carrier To the formulation of Example 4, approximately 300 micrograms pure lavender oil was added, giving a concentration of pure lavender oil of 0.0003% (wt.) The resulting formulation had a barely detectable scent of lavender, which served to mask the faint scent of grape seed oil.

Example 6—Treatments Using Inventive Formulation

[a] Subject 1, a 38-year old male, had a pre-existing slight cystic acne condition. The subject used about 8 drops of a formulation consisting of HG2-V1 dissolved in grape-seed oil in a concentration of 0.4% (wt.), with no other components in the formulation, applied to the face each night before bed-time after washing the face with soap. The subject used no other products on the skin. In addition, 2-3 drops were applied to any existing acne lesions once in the morning. The subject applied the formulation for a total of 3 months. The subject observed a noticeable increase in the healing rate of the acne lesions compared to no use of the formulation, and the acne lesions were smaller and shorter-lived than without the formulation. The subject noticed fewer new acne lesions after using the formulation. The subject noticed less scarring from the acne lesions compared to no use of the formulation. In addition, the subject noted that areas of the facial skin unaffected by acne felt healthier due to increased skin thickness. The subject noted no increased photosensitivity (i.e., no increased erythema or light sensitivity) compared to no use of the formulation. The subject repeated the test for 2 months with a similar formulation, where the only difference was that the active was HG2-V2. Similar results were observed for the HG2-V2 formulation. The results show that fullerene-derived keto-lactams have antioxidant and/or ameliorative properties of the inflammation of acne, improve the appearance of cystic acne and the severity of scarring associated with cystic acne, as well as prevent the appearance of new acne lesions.

[b] Subject 2, a 34-year old female, had generally healthy skin, with no wrinkles, and only slight periodic appearance of small (non-cystic) acne lesions. The subject used about 8 drops of a formulation consisting of HG2-V1 dissolved in grape-seed oil in a concentration of 0.4% (wt.).), with no other components in the formulation, applied to the face each night before bed-time after washing the face with soap. In addition, about 6 drops were applied to the face each morning. The subject used no other products on the skin. The subject used the formulation for a total of 3 months. The subject before beginning use of the formulation also had dryness around the chin region of the face. The subject observed a noticeable decrease in the appearance of small acne lesions. The healing rate of the acne lesions that did occur was increased compared to no use of the formulation. The dryness of the chin area was decreased. The subject also noticed an improved healthiness of the skin through the general appearance of a healthy sheen.

No increase in photosensitivity was observed. The results show that the compounds of the present invention act as antioxidants, and/or inflammation ameliorative agents, have no noticeable photosensitizing effect or other undesirable side-effect, and prevent and reduce the appearance of common, slight acne. The formulation also acted as a moisturizing agent as well as providing an improvement in the overall appearance and health of the skin.

[c] 25 human subjects, for which the minimal erythemal dose (MED) of full spectrum UV light (Solar Light Company's 601-300 Multiport Simulator, emitting light of a Xenon-Shortarc Lamp) had been determined, were treated with 6 occluded patches (on the back) with a formulation of HG2-V2 (0.3% wt.) in grape seed oil. 24 hours after patch treatment, the regions of application were exposed to 3×MED of the same light source. Subjects had an average erythemic response for all subjects over all data points of 0.77 on the erythema response scale, where 1 is the first sign of erythema (corresponding to 1×MED). This provides evidence that the formulation provided an anti-erythemic effect, since erythema scores for 3×MED should range between 1-3. In addition, these results demonstrate that the net generation of $^1O_2$ under conditions of typical use and UV exposure is not significant, and that HG2-V2 has the effect of a net reduction in reactive oxygen species which are typically formed in the skin upon UV exposure.

[d] A percutaneous absorption study was conducted with 6 fresh viable skin samples from one donor, where 20 times recommended usage level (recommended usage level is 6-8 drops on the face) of a 0.3% (wt.) formulation of HG2-V2 in grape seed oil was used. Analysis by extraction of receptor fluid with toluene and analysis with HPLC-MS (using Buckyprep analytical column) was performed. Receptor fluid at 8 hr and 24 hr collection points showed all samples to contain no HG2-V2 at or above analytical detection limit, corresponding to less than 0.004% absorption, showing that HG2-V2 is not absorbed into the bloodstream in any significant amount.

Example 7—Synthesis of KetoEster1

Synthesis of Methyl 11-Bromoundecanoate

A mixture of 13.25 g of 11-bromoundecanoic acid, 100 mL of methanol and 10 drops of hydrochloric acid was stirred for 3 days in a closed flask. The solvent was removed in vacuo and the residual oil was redissolved in ether (100 mL). This solution was subsequently washed twice with 25 mL of a saturated $NaHCO_3$ solution, once with water (25 mL) and once with brine (25 mL). Drying over sodium sulfate and removal of the solvents in vacuo gave 13.32 g of the product as a yellowish oil, which was sufficiently pure to use in the next step. $^1H$ NMR (200 MHz, $CDCl_3$): δ 3.65 (s, 3H); 3.39 (t, 2H); 2.28 (t, 2H); 1.90-1.78 (m, 2H); 1.70-1.50 (m, 2H); 1.50-1.21 (m, 12H) ppm. IR (neat, $cm^{-1}$): 2928 (m); 2855 (m); 1741 (s).

Synthesis of 11-Azido-Undecanoic Acid Methyl Ester

A mixture of 13.3 g of methyl 11-bromoundecanoate and 3.12 g of sodium azide in 50 mL of DMSO was heated at 66° C. under nitrogen for 2 days. The reaction mixture was cooled down and mixed with 200 mL of ice water. The aqueous layer was extracted with ether (1×100 mL, subsequently 3×50 mL). The organic layers were combined, washed twice with 25 mL of brine and dried over $Na_2SO_4$. Removal of the solvents in vacuo gave 11.2 g of a yellow oil. Purification by column chromatography (silica gel; petroleum ether (40-60° C.)/ether=9:1 (v/v)) gave 10.94 g of the pure product as a colorless oil, which was stored at 4° C. to prevent degradation. $^1H$ NMR (300 MHz, $CDCl_3$): δ 3.65 (s, 3H); 3.24 (t, 2H, J=7.0 Hz); 2.29 (t, 2H, J=7.5 Hz); 1.65-1.53 (m, 2H); 1.42-1.21 (m, 14H) ppm. $^{13}C$ NMR (75 MHz, $CDCl_3$): δ 174.24; 51.44; 51.37; 34.04; 29.35; 29.27; 29.15; 29.07; 28.80; 26.66; 24.89 ppm. IR (neat, $cm^{-1}$): 2929 (m); 2856 (m); 2096 (s); 1741 (s).

Synthesis of KetoEster1

A solution of 2.16 g of $C_{60}$ in 200 mL of ortho-dichlorobenzene (ODCB) was heated under $N_2$ to 90° C. A solution of 730 mg of 11-azido-undecanoic acid methyl ester in 20 mL of ODCB was added dropwise over 1 h. The reaction mixture was kept at 90° C. for 2 h, subsequently heated to 110° C., and allowed to react overnight at 110° C. The reaction mixture was cooled down and concentrated in vacuo. The residue was redissolved in 50 mL of ODCB and the crude azafulleroid derivative was isolated by column chromatography (silica gel; toluene).

Figure 14:
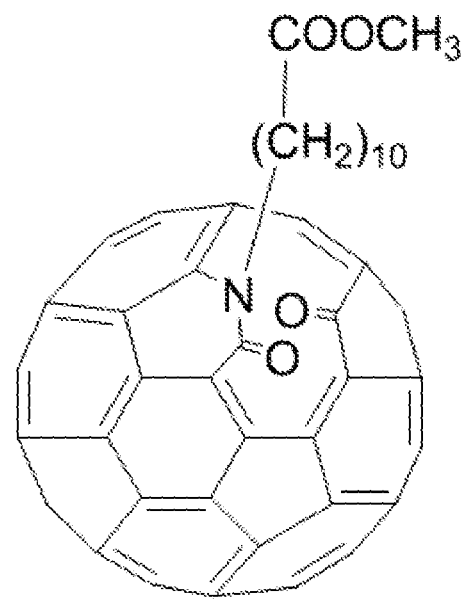
FIG. 14 depicts fullerene-derived ketolactam KetoEster1.

The crude azafulleroid was redissolved in 100 mL of ODCB and this solution was illuminated overnight with a 150 W sodium flood lamp, while bubbling oxygen through the solution. The solvent was removed in vacuo. The crude product was isolated by column chromatography (silica gel; toluene/ethyl acetate=96/4 (v/v)) and further purified by a second column chromatography (silica gel; toluene/ethyl acetate=99/1 (v/v)). The obtained material was redissolved in toluene, precipitated into pentane and isolated by centrifugation. The brown solid was washed twice with pentane and dried in vacuo. This gave 165 mg of KetoEster1 (FIG. 14). $^1H$ NMR (300 MHz, $CDCl_3$): δ 5.24-5.14 (m, 1H); 4.35-4.26 (m, 1H); 3.66 (s, 3H); 2.30 (t, 2H, J=7.5 Hz); 2.05-1.90 (m, 2H); 1.70-1.20 (m, 14H) ppm. IR (KBr, $cm^{-1}$): 2924 (m); 2850 (m); 2366 (w); 1727 (s); 1687 (s); 1558 (m); 522 (m).

Figure 15:
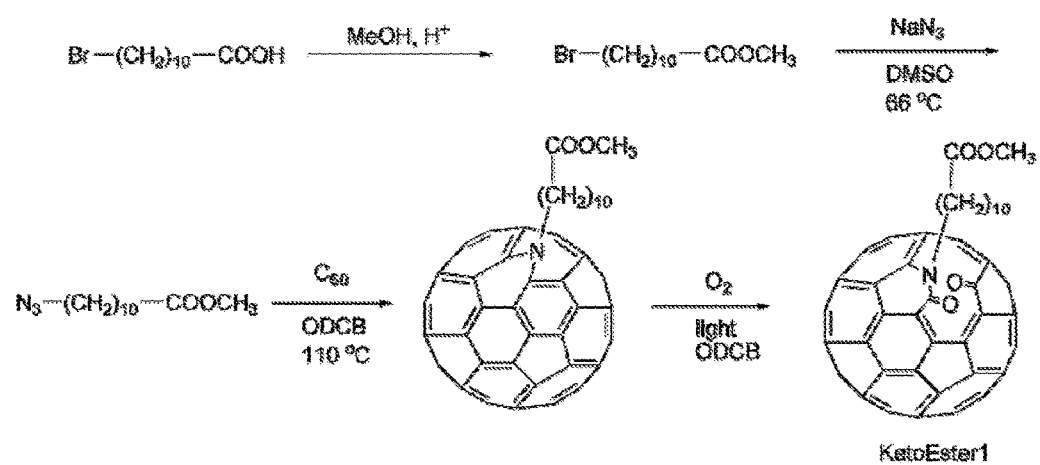
FIG. 15 depicts one possible synthetic scheme for KetoEster1.

A scheme of one possible KetoEster1 synthesis protocol is depicted in FIG. 15.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A cosmetic or dermatological composition, comprising:
a $C_x$ fullerene-derived ketolactam of formula I; and
a cosmetically or dermatologically acceptable carrier;
wherein
the composition has an absorbance value of greater than about 0.1 at a wavelength of 570 nm; and
the $C_x$ fullerene-derived ketolactam of formula I is

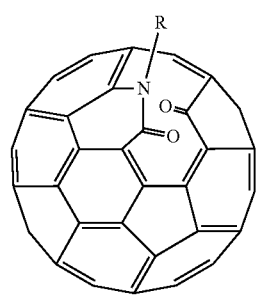

I wherein x is 60, 70, 76, 78, 84, or 90;
R is a $C_1$-$C_{50}$ hydrocarbon chain, branched or unbranched, with unsaturation from zero up to maximal, optionally substituted with an aryl group, heteroaryl group, halogen atom, hydroxyl group, a branched or unbranched, with unsaturation from zero up to maximal alkoxy group, or a branched or unbranched, with unsaturation from zero up to maximal alkanoyloxy group, said aryl or heteroaryl being optionally substituted with two or more groups, independently selected from the group consisting of halogen atoms, hydroxyl groups, $C_1$-$C_{50}$ hydrocarbon chains, branched or unbranched, with unsaturation from zero up to maximal alkyl group, $C_1$-$C_{50}$, branched or unbranched, with unsaturation from zero up to maximal alkoxy groups, $C_1$-$C_{50}$, branched or unbranched, with unsaturation from zero up to maximal alkanoyloxy groups, or —O(CH$_2$CH$_2$O)$_n$R' groups;

n is 1 to 100 inclusive; and

R' is H, aryl, or a $C_1$-$C_{50}$ hydrocarbon chain, branched or unbranched, with unsaturation from zero up to maximal.

2. The composition of claim 1, wherein the $C_x$ fullerene-derived ketolactam of formula I is represented by formula III:

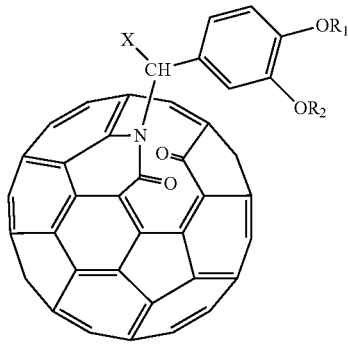

III wherein x is 60, 70, 76, 78, 84, or 90;

X is H or a $C_1$-$C_{50}$ linear or branched, with unsaturation from zero up to maximal alkyl group;

$R_1$ is H, a $C_1$-$C_{50}$ linear or branched, with unsaturation from zero up to maximal alkyl group, or O(CH$_2$CH$_2$O)$_m$R'';

m is 1 to 100 inclusive;

R'' is H, aryl, or a $C_1$-$C_{50}$ hydrocarbon chain, branched or unbranched, with unsaturation from zero up to maximal;

$R_2$ is H, a $C_1$-$C_{50}$ linear or branched, with unsaturation from zero up to maximal alkyl group, or O(CH$_2$CH$_2$O)$_p$R''';

p is 1 to 100 inclusive; and

R''' is H, aryl, or a $C_1$-$C_{50}$ hydrocarbon chain, branched or unbranched, with unsaturation from zero up to maximal.

3. The composition of claim 2, wherein X is H or alkyl; $R_1$ is $C_{10}$-$C_{24}$ alkyl; and $R_2$ is CH$_3$.

4. The composition of claim 2, wherein X is H; $R_1$ is a $C_{16}$ alkyl; and $R_2$ is CH$_3$.

5. The composition of claim 1, wherein the $C_x$ fullerene-derived ketolactam of formula I is CAS#943912-75-2, or 2a-Aza-1,2(2a)-homo-1,9-seco[5,6]fullerene-C$_{60}$-I$_h$-1,9-dione,2a-[[4-docosyloxy)-3-methoxyphenyl]methyl].

6. The composition of claim 1, wherein the $C_x$ fullerene-derived ketolactam of formula I further comprises:

(a) one or more additional addends, each of which is fused to the fullerene cage at a distinct pair of adjacent carbon atoms in the fullerene cage; wherein each of the one or more additional addends is independently selected from the group consisting of a —C(Y)(Z)— group, a —C(R$_4$R$_5$)—N(R$_3$)—C(R$_6$R$_7$)— group, and an oxygen atom;

wherein Y and Z each independently represent optionally substituted aryl or alkyl;

$R_6$ represents optionally substituted aryl or aralkyl; and $R_3$, $R_4$, $R_5$, and $R_7$ are each independently optionally substituted alkyl, cycloalkyl, heteroalkyl, heterocycloalkyl, alkenyl, or aralkyl; or (b) an azafulleroid modification of the fullerene cage.

7. The composition of claim 1, wherein the composition has an absorbance value of greater than about 0.25 at a wavelength of 570 nm.

8. A $C_x$ fullerene-derived ketolactam of formula I

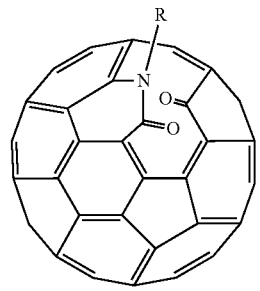

I wherein x is 60, 70, 76, 78, 84, or 90;

R is a $C_1$-$C_{50}$ hydrocarbon chain, branched or unbranched, with unsaturation from zero up to maximal, optionally substituted with an aryl group, heteroaryl group, halogen atom, hydroxyl group, a branched or unbranched, with unsaturation from zero up to maximal alkoxy group, or a branched or unbranched, with unsaturation from zero up to maximal alkanoyloxy group, said aryl or heteroaryl being optionally substituted with two or more groups, independently selected from the group consisting of halogen atoms, hydroxyl groups, $C_1$-$C_{50}$ hydrocarbon chains, branched or unbranched, with unsaturation from zero up to maximal alkyl group, $C_1$-$C_{50}$, branched or unbranched, with unsaturation from zero up to maximal alkoxy groups, $C_1$-$C_{50}$, branched or unbranched, with unsaturation from zero up to maximal alkanoyloxy groups, or —O(CH$_2$CH$_2$O)$_n$R' groups;

n is 1 to 100 inclusive; and

R' is H, aryl, or a $C_1$-$C_{50}$ hydrocarbon chain, branched or unbranched, with unsaturation from zero up to maximal, further comprising:

(a) one or more additional addends, each of which is fused to the fullerene cage at a distinct pair of adjacent carbon atoms in the fullerene cage; wherein each of the one or more additional addends is independently selected from the group consisting of a —C(Y)(Z)— group, a —C(R$_4$R$_5$)—N(R$_3$)—C(R$_6$R$_7$)— group, and an oxygen atom;

wherein Y and Z each independently represent optionally substituted aryl or alkyl;

$R_6$ represents optionally substituted aryl or aralkyl; and $R_3$, $R_4$, $R_5$, and $R_7$ are each independently optionally substituted alkyl, cycloalkyl, heteroalkyl, heterocycloalkyl, alkenyl, or aralkyl; or (b) an azafulleroid modification of the fullerene cage.

9. The $C_x$ fullerene-derived ketolactam of claim 8, wherein the $C_x$ fullerene-derived ketolactam of formula I is represented by formula III:

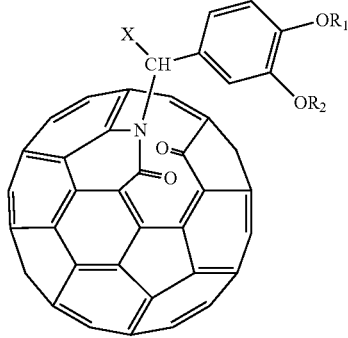

III

X is H or a $C_1$-$C_{50}$ linear or branched, with unsaturation from zero up to maximal alkyl group;

$R_1$ is H, a $C_1$-$C_{50}$ linear or branched, with unsaturation from zero up to maximal alkyl group, or $O(CH_2CH_2O)_m R''$;

m is 1 to 100 inclusive;

R" is H, aryl, or a $C_1$-$C_{50}$ hydrocarbon chain, branched or unbranched, with unsaturation from zero up to maximal;

$R_2$ is H, a $C_1$-$C_{50}$ linear or branched, with unsaturation from zero up to maximal alkyl group, or $O(CH_2CH_2O)_p R'''$;

p is 1 to 100 inclusive; and

R''' is H, aryl, or a $C_1$-$C_{50}$ hydrocarbon chain, branched or unbranched, with unsaturation from zero up to maximal.

10. The $C_x$ fullerene-derived ketolactam of claim 9, wherein X is H or alkyl; $R_1$ is $C_{10}$-$C_{24}$ alkyl; and $R_2$ is $CH_3$.

11. The $C_x$ fullerene-derived ketolactam of claim 9, wherein X is H; $R_1$ is a $C_{16}$ alkyl; and $R_2$ is $CH_3$.

12. The $C_x$ fullerene-derived ketolactam of claim 9, wherein x is 60; X is H; $R_1$ is a $C_{22}$ alkyl; and $R_2$ is $CH_3$.

13. The $C_x$ fullerene-derived ketolactam of claim 8, wherein the one or more additional addends or modification is an azafulleroid modification of the fullerene cage.

14. The $C_x$ fullerene-derived ketolactam of claim 8, wherein x is 60.

15. The $C_x$ fullerene-derived ketolactam of claim 9, wherein x is 60.

16. The $C_x$ fullerene-derived ketolactam of claim 10, wherein x is 60.

17. The $C_x$ fullerene-derived ketolactam of claim 11, wherein x is 60.

* * * * *